(12) United States Patent
Tekeste et al.

(10) Patent No.: US 10,149,949 B2
(45) Date of Patent: Dec. 11, 2018

(54) DRUG DELIVERY CONNECTORS

(71) Applicant: Becton, Dickinson and Company, Franklin Lakes, NJ (US)

(72) Inventors: Girum Yemane Tekeste, Hackensack, NJ (US); Richard Giddes, Edison, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/230,861

(22) Filed: Aug. 8, 2016

(65) Prior Publication Data

US 2016/0339184 A1 Nov. 24, 2016

Related U.S. Application Data

(62) Division of application No. 13/210,767, filed on Aug. 16, 2011, now Pat. No. 9,433,768.

(60) Provisional application No. 61/467,465, filed on Mar. 25, 2011.

(51) Int. Cl.
*A61M 5/34* (2006.01)
*A61M 5/31* (2006.01)
*A61M 39/10* (2006.01)

(52) U.S. Cl.
CPC .......... *A61M 5/348* (2013.01); *A61M 5/3134* (2013.01); *A61M 5/34* (2013.01); *A61M 39/10* (2013.01); *A61M 2039/1077* (2013.01); *A61M 2039/1094* (2013.01)

(58) Field of Classification Search
CPC ...... A61M 5/3134; A61M 5/34; A61M 5/346; A61M 5/347; A61M 39/10; A61M 2039/1077; A61M 2039/1094
See application file for complete search history.

(56) References Cited

U.S. PATENT DOCUMENTS

| 3,043,304 A | 7/1962 | Higgins |
| 3,472,227 A | 10/1969 | Burke |
| 4,538,836 A | 9/1985 | Krütten |

(Continued)

FOREIGN PATENT DOCUMENTS

| AU | 2010202231 B2 | 1/2011 |
| CA | 2483178 A1 | 11/2003 |

(Continued)

OTHER PUBLICATIONS

Final Office Action in U.S. Appl. No. 13/210,767, dated Mar. 27, 2015, 9 pages.

(Continued)

*Primary Examiner* — Kami A Bosworth
(74) *Attorney, Agent, or Firm* — Servilla Whitney LLC

(57) ABSTRACT

Devices having male connectors for preventing connection to non-compatible female connectors are described. An exemplary male connector includes an elongate tip and a collar disposed coaxially around the elongate tip including a plurality of ribs disposed on either an inside surface or an outside surface of the collar for preventing entry of a non-compatible female connector into a channel formed between the elongate tip and the collar. One or more embodiments pertain to a device with a male connector and a compatible female connector including a threaded portion for engaging a corresponding threaded portion of the male connector.

12 Claims, 20 Drawing Sheets

(56) References Cited

U.S. PATENT DOCUMENTS

| | | | |
|---|---|---|---|
| 4,740,205 A | 4/1988 | Seltzer et al. | |
| 5,069,225 A | 12/1991 | Okamura | |
| 5,437,650 A | 8/1995 | Larkin et al. | |
| 5,484,421 A | 1/1996 | Smocer | |
| 5,509,911 A | 4/1996 | Cottone, Sr. et al. | |
| 5,545,152 A | 8/1996 | Funderburk et al. | |
| 5,569,222 A | 10/1996 | Haselhhorst et al. | |
| 5,573,516 A | 11/1996 | Tyner | |
| 5,616,133 A | 4/1997 | Cardenas | |
| 5,616,136 A | 4/1997 | Shillington | |
| 5,968,020 A | 10/1999 | Saito | |
| 6,050,978 A | 4/2000 | Orr et al. | |
| 6,273,870 B1 | 8/2001 | Garvin | |
| 6,402,207 B1 | 6/2002 | Segal | |
| 6,500,153 B1 | 12/2002 | Sheppard et al. | |
| 6,508,807 B1 | 1/2003 | Peters | |
| 6,599,269 B1 | 7/2003 | Lewandowski et al. | |
| 6,612,624 B1 | 9/2003 | Segal et al. | |
| 7,040,598 B2 | 5/2006 | Raybuck | |
| 7,137,654 B2 | 11/2006 | Segal | |
| 7,306,566 B2 | 12/2007 | Raybuck | |
| 7,651,481 B2 | 1/2010 | Raybuck | |
| 7,873,402 B2 | 1/2011 | Schachar et al. | |
| 2003/0212372 A1 | 11/2003 | Bills et al. | |
| 2005/0251096 A1 | 11/2005 | Armstrong et al. | |
| 2006/0033331 A1 | 2/2006 | Ziman | |
| 2006/0047251 A1 | 3/2006 | Bickford Smith et al. | |
| 2007/0060898 A1 | 3/2007 | Shaughnessy et al. | |
| 2007/0076401 A1 | 4/2007 | Carrez et al. | |
| 2007/0179454 A1 | 8/2007 | Ziman et al. | |
| 2007/0260195 A1 | 11/2007 | Bartholomew et al. | |
| 2008/0045929 A1 | 2/2008 | Birnbach | |
| 2008/0103486 A1 | 5/2008 | Owens | |
| 2008/0132851 A1* | 6/2008 | Shaw | A61M 5/347 604/199 |
| 2008/0312640 A1* | 12/2008 | Grant | A61M 39/10 604/533 |
| 2008/0319422 A1 | 12/2008 | Cardenas | |
| 2009/0099552 A1 | 4/2009 | Levy et al. | |
| 2009/0187166 A1 | 7/2009 | Young | |
| 2009/0326481 A1 | 12/2009 | Swisher et al. | |
| 2010/0286558 A1 | 11/2010 | Schraga | |
| 2012/0245564 A1 | 9/2012 | Tekeste et al. | |

FOREIGN PATENT DOCUMENTS

| | | |
|---|---|---|
| CA | 2588888 A1 | 6/2006 |
| CA | 2612094 A1 | 12/2006 |
| CA | 2692157 A1 | 12/2008 |
| CA | 2735146 A1 | 3/2010 |
| CN | 1299686 A | 6/2001 |
| DE | 102006050212 A1 | 4/2008 |
| EP | 0716860 A2 | 6/1996 |
| EP | 2269685 A2 | 1/2011 |
| FR | 2928552 A1 | 9/2009 |
| JP | S58-13216 A | 1/1983 |
| JP | H09-507779 A | 8/1997 |
| JP | 2001187141 A | 7/2001 |
| JP | 2002500935 A | 1/2002 |
| JP | 2007098106 A | 4/2007 |
| JP | 2007512855 A | 5/2007 |
| JP | 2009544345 A | 12/2009 |
| WO | 99/37356 A1 | 7/1999 |
| WO | 2008/009946 A1 | 1/2008 |
| WO | 2009/144583 A1 | 12/2009 |
| WO | 2010/064074 A1 | 6/2010 |

OTHER PUBLICATIONS

Final Office Action in U.S. Appl. No. 13/210,767, dated Nov. 25, 2013, 9 pgs.
Final Office Action in U.S. Appl. No. 13/210,966, dated Apr. 28, 2015, 13 pages.
Final Office Action in U.S. Appl. No. 13/210,966, dated May 30, 2014, 12 pages.
Final Office Action in U.S. Appl. No. 13/210,966 dated Aug. 1, 2016, 13 pages.
IPRP in International No. PCT/US2011/048057, dated Oct. 10, 2013, 8 pgs.
Non-Final Office Action in U.S. Appl. No. 13/210,767, dated Nov. 18, 2014, 12 pages.
Non-Final Office Action in U.S. Appl. No. 13/210,767, dated Jul. 19, 2013, 13 pgs.
Non-Final Office Action in U.S. Appl. No. 13/210,966, dated Nov. 17, 2014, 10 pages.
Non-Final Office Action in U.S. Appl. No. 13/210,966, dated Nov. 25, 2013, 15 pgs.
IPRP in International No. PCT/US2011/048034, dated Feb. 19, 2013, 6 pgs.
PCT International Search Report & Written Opinion in PCT/US2011/048034, dated Dec. 15, 2011, 11 pgs.
PCT International Search Report & Written Opinion in PCT/US2011/048057, dated Dec. 14, 2011, 10 pgs.
Non-Final Office Action in U.S. Appl. No. 13/210,966 dated Jan. 6, 2017, 15 pages.
Extended European Search Report in 16204426.7 dated May 2, 2017, 10 pages.
Extended European Search Report in EP 17203747.5 dated Mar. 1, 2018, 6 pages.

* cited by examiner

DRUG DELIVERY CONNECTORS

CROSS-REFERENCE TO RELATED APPLICATIONS

This application is a divisional of U.S. patent application Ser. No. 13/210,767, filed Aug. 16, 2011, which issued on Sep. 6, 2016 as U.S. Pat. No. 9,433,768, which claims priority under 35 U.S.C. § 119(e) to U.S. Provisional Application No. 61/467,465, filed Mar. 25, 2011, the disclosures of which are incorporated herein by reference in their entirety.

TECHNICAL FIELD

Aspects of the present invention relate to drug delivery devices and connectors that prevent misconnection with non-compatible connectors.

BACKGROUND

Connectors used with drug delivery devices typically share a common ISO standard luer connection. A standard male luer tip or standard male connector has specifications as provided by the International Organization for Standardization (ISO) in ISO 594-1:1986 and 594-2:1998, including a 6% taper that increases from the open distal end to the proximal end and an outer cross-sectional diameter at the distal end of the tip measuring between about 0.1545 inches (3.925 mm) and about 0.1570 inches (3.990 mm) for rigid material and between about 0.1545 inches (3.925 mm) and about 0.1585 inches (4.027 mm) for semi-rigid material. A standard female luer hub or standard female luer connector may have a 6% taper that decreases from the open proximal end to the distal end and an inner cross-sectional diameter at the open proximal end measuring between about 0.168 inches (4.270 mm) to about 0.170 inches (4.315 mm). In embodiments of standard female luer connectors that incorporate tabs or lugs for connection to a corresponding male luer lock connector, the outer cross-sectional diameter of the standard female luer connector, including the lugs, is in the range from about 0.307 inches (7.80 mm) to about 0.308 inches (7.83 mm). In embodiments of standard female luer connectors that do not incorporate tabs or lugs for connection to a corresponding male luer lock connector, the outer cross-sectional diameter may be about 0.224 inches (5.700 mm) for rigid connectors and about 0.265 inches (6.730 mm) for semi-rigid connectors, based on the maximum outside diameter of the standard female luer connector at the base of the lugs of ISO 594-2. The minimum length of the standard luer tip and/or the standard luer hub is 0.295 inches (7.500 mm), according to ISO 594-1. As used herein, the phrases "standard male luer connector," "standard male luer tip," "standard female luer hub" and "standard female luer connector" shall refer to connectors having the above dimensions. Connectors that do not have the above dimensions shall be referred to as non-luer connectors.

Standard luer male connectors and standard luer female connectors, collectively referred to herein as standard luer connectors, may be used in intravascular, anesthesia and enteral delivery systems and may include structure that allows a drug delivery device for one system to be to be compatible with other systems. For example, some neuraxial drug delivery systems may use the same type of standard luer connector as the connectors used with other delivery applications, for example, central intravenous catheters, central venous pressure parts, infusion ports, balloon ports, introducer ports, IV luer connectors, peritoneal dialysis catheters, distal port for a pulmonary artery catheter, and many other connectors. An unintended consequence of connecting a drug delivery device for one type of delivery system to connectors for use with other types of delivery systems is that such connection would provide a link between two unrelated systems, i.e., neuraxial to intravenous (IV). Each delivery system is intended to provide unique methods of delivery, with distinctly different purposes and different medications, which the interchangeability of known drug delivery systems can circumvent. Such circumvention can lead to harm and/or serious injury to the patient.

Limiting the use of standard luer connectors for vascular access or systems is one consensus accepted by device manufacturers and regulatory bodies. Accordingly, there has been a need to modify all other devices so they have a different type of connector that cannot physically connect with a standard luer connector or incompatible devices. New proposed standards for small bore connectors, for example ISO 80369-6 for neuraxial applications, have also propelled the need for suitable connectors that do not conform to standard luer connector requirements or non-luer connectors. These new proposed standards include connectors with a 5% taper, instead of a 6% taper that is currently used with standard luer connectors. In addition, the new standards propose connectors with smaller inner and outer cross-sectional diameters and longer lengths than standard luer connectors.

Attempts to prevent or minimize misconnections between drug delivery systems include educating practitioners about misconnections, labeling and color-coding. However, these attempts offer only temporary solutions. Use of non-luer connections alone does not ensure that a misconnection cannot be made, as a male tip and a female hub can often be forced together even if the dimensions are not complementary.

There is a need for connectors for use with drug delivery systems that prevent misconnection with non-compatible connectors used with unintended drug delivery systems.

SUMMARY

In this disclosure, a convention is followed wherein the distal end of the device is the end closest to a patient and the proximal end of the device is the end away from the patient and closest to a practitioner.

A first aspect of the present invention pertains to a device or a drug delivery device comprising an open elongate tip for connection to a compatible female connector and a collar disposed coaxially around the elongate tip and forming a channel between the elongate tip and the collar for receiving a portion of the compatible female connector. In one or more embodiments, the collar includes a plurality of longitudinal ribs which prevent the entry of a non-compatible female connector into the channel and prevent connection of the non-compatible female connector to the open elongate tip.

The term "non-compatible" with respect to male and female connectors refers to a connector having a shape, size, dimension or structure that prevents connection to another connector. For example, a luer female connector has a shape, size, dimension and/or structure that prevents it from forming a connection with a non-luer male connector and is thus a non-compatible connector with respect to the non-luer male connector. Such a luer female connector, however, has a shape, size, dimension and/or structure that permits formation of a connection with a luer male connector and is, thus, a compatible connector with respect to the luer male connector. In another example, a non-luer female connector has a shape, size, dimension and/or structure that prevents formation of a connection with a luer male connector and is, thus, a non-compatible connector with respect to the luer male connector. Such a non-luer female connector has a shape, size dimension and/or structure that permits formation of a connection with a non-luer male connector and is, thus a compatible connector with respect to the non-luer male connector.

As used herein, the term "dimension" shall include the length, diameter or width of a geometric shape or the geometrically shaped components described herein. The term "cross-sectional diameter" shall include the measurement of the longest distance or greatest distance between two points on an edge of a cross-section of an object or component with a circular or non-circular cross-section. The two points may be located on the inside surface or outside surface of the edge of the cross-section of the object. The cross-sectional diameter of two points located on the inside surface of the edge of the cross-section of the object shall be referred to as the "inside cross-sectional diameter" and the cross-sectional diameter of two points located on the outside surface of the edge of the cross-section of an object shall be referred to as the "outside cross-sectional diameter." It should be recognized that "cross-sectional diameter" of objects having a circular cross-section may be referred to as the "cross-sectional dimension" or "diameter" of the object. The terms "cross-sectional dimension," "cross-sectional diameter" and "diameter" may be used interchangeably for objects having a circular cross-section.

In one or more embodiments, the compatible female connector includes a non-luer connector, as defined herein, and the non-compatible female connector includes a standard luer connector, as defined herein. In one or more alternative embodiments, the compatible female connector includes a standard luer connector and the non-compatible female connector includes a non-luer connector.

In one or more embodiments, the collar disposed coaxially around the open elongate tip includes a proximal end, a distal end and the plurality of longitudinal ribs extend from the proximal end to the distal end of the collar.

In one variant, the plurality of longitudinal ribs are disposed on an inside surface of the collar. Such longitudinal ribs extend inwardly into the channel formed between the collar and the elongate tip. In one or more such embodiments, the plurality of ribs define an inner cross-sectional diameter that is less than the inner cross-sectional diameter of non-compatible female connector, which may include a standard luer connector and the collar at an outer surface defines an outer cross-sectional diameter that is greater than about 0.168 inches.

In another variant, the plurality of longitudinal ribs is disposed on the outside surface and extends outwardly therefrom. In such embodiments, the longitudinal ribs define an outer cross-sectional diameter that is greater than about 0.168 inches and the collar at the inside surface defines an inner cross-sectional diameter that is less than the outer cross-sectional diameter of a non-compatible female connector, which may include a standard luer connector.

In one or more embodiments, the device may include a container having an open distal end including a distal wall and a sidewall extending in the proximal direction from the distal wall. The sidewall may include an inside surface that defines a chamber for retaining fluids. In such embodiments, the elongate tip of the device extends in a distal direction from the distal wall and provides access to the chamber or provides fluid communication with the chamber at the distal end.

A second aspect of the present invention pertains to a drug delivery kit. In one or more embodiments, the kit may include a device or drug delivery device as otherwise described herein and a compatible female connector for removable attachment to the elongate tip of the devices described herein. In one or more embodiments of the kit, the collar of the device is integrally formed on the device. In one variant of the second aspect of the present invention, the compatible female connector may include an open distal end, an open proximal end in fluid communication with the open distal end.

In one or more embodiments, the compatible female connector may include an attachment portion including an interior surface defining an inner dimension. The inner dimension of the attachment portion may be sized to attach the compatible female connector to the elongate tip in a fluid-tight connection, or, in other words, enable a fluid-tight connection between the compatible female connector and the elongate tip of the device. The interior surface of the attachment portion may include a taper of less than 6% decreasing in a proximal to distal direction. The interior surface of one or more embodiments may define a cavity with an inner cross-sectional diameter sized to prevent connection of the compatible female connector to a standard male connector.

The attachment portion of the compatible female connector may include an exterior surface and a threaded portion disposed thereon. The length of the threaded portion may be equal to or greater than the length of the collar of the device.

A third aspect of the present invention pertains to a connector including a collar disposed coaxially around a distally extending standard male luer tip. The collar may include an open distal end and a proximal end for attachment to a container. The proximal end of the collar may comprise a standard female hub connector that is compatible or can attach to a standard male luer connector.

The collar may also form a channel with the standard male luer tip such that the channel is disposed between the non-standard male luer tip and the collar. In one or more embodiments, the collar may include plurality of longitudinal ribs that prevent entry of a non-compatible female connector into the channel and connection thereof to the standard male luer tip. The plurality of ribs may extend from the open distal end of the collar to the proximal end of the collar.

In one or more embodiments, the collar includes an inside surface on which the plurality of longitudinal ribs are disposed. The plurality of ribs may define an inner cross-sectional diameter. In another variant, the collar includes an outside surface on which the plurality of ribs is disposed. The plurality of ribs may define an outer cross-sectional diameter. The inner cross-sectional diameter and/or the outer cross-sectional diameter of the collar may be sized and/or shaped to prevent entry of the non-compatible female connector into the channel and connection thereof to the standard male luer tip. In one or more alternative embodiments, the inside surface may include a threaded portion and may further be free of any ribs. In such embodiments, the plurality of ribs may be disposed on the outside surface of the collar.

The devices and kits of one or more embodiments described herein may be used for neuraxial, anesthesia, intravascular or other drug delivery applications.

DETAILED DESCRIPTION

Figure 1:
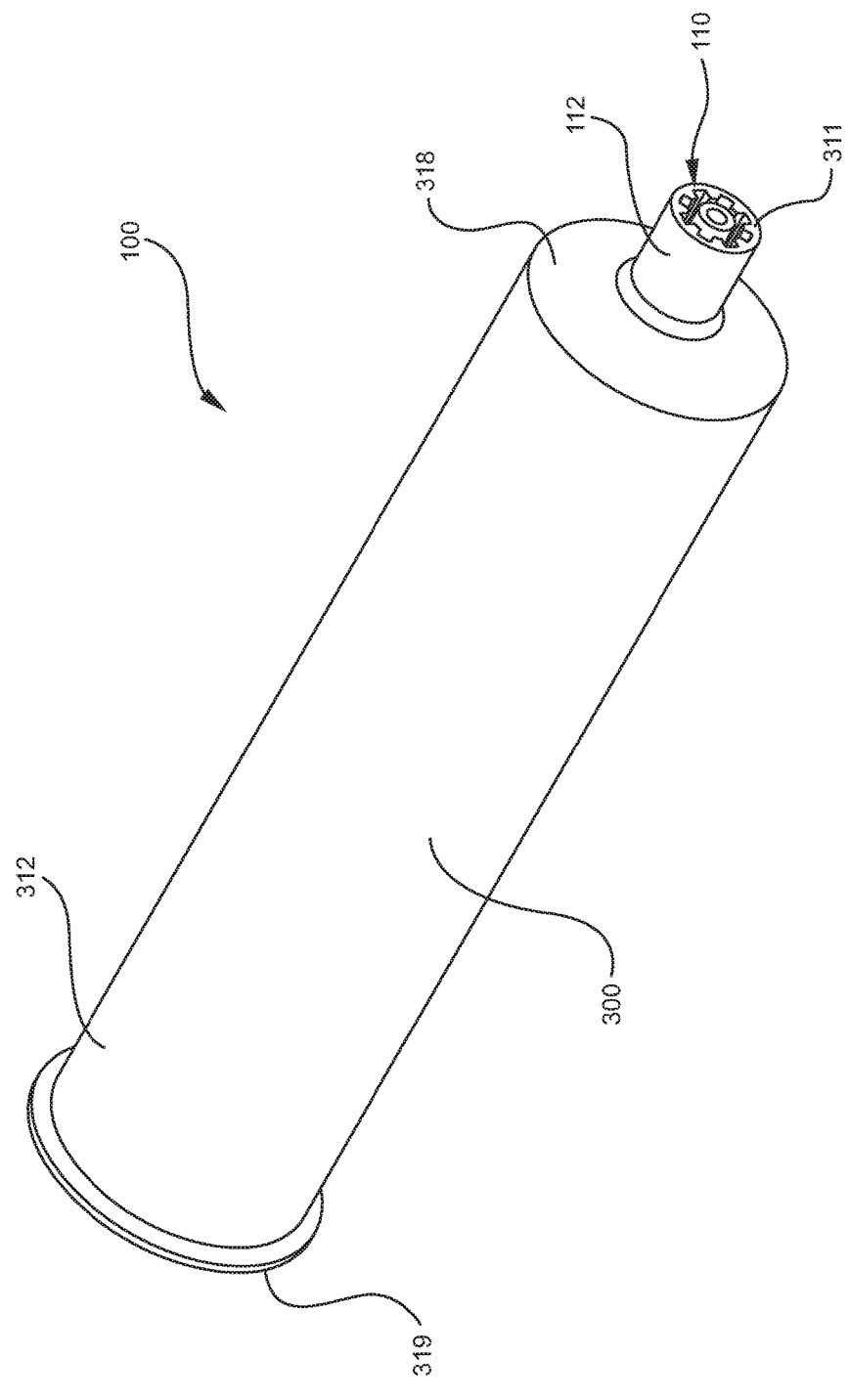
FIG. 1 illustrates a perspective view of a connector according to one or more embodiments.
Figure 2:
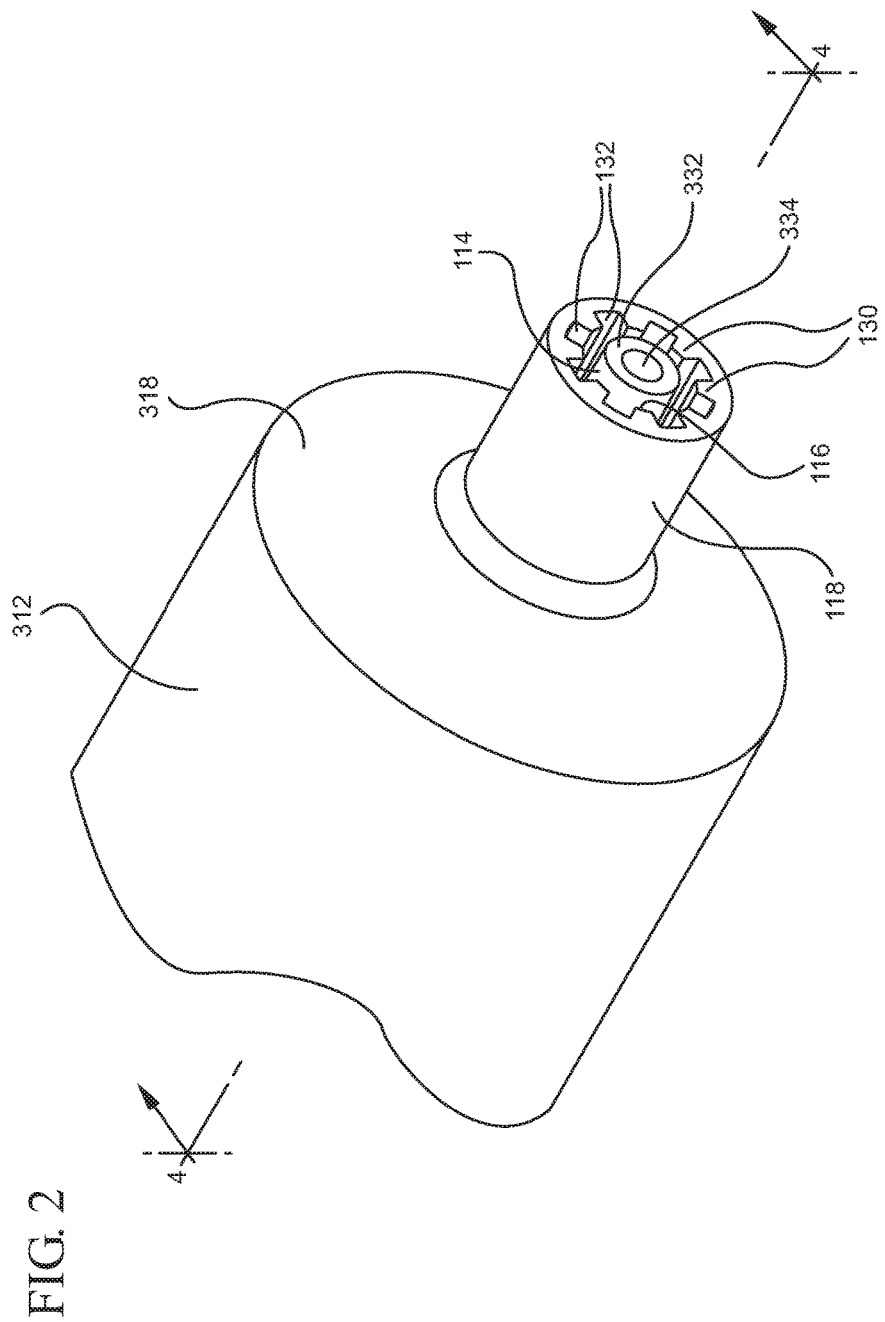
FIG. 2 illustrates an enlarged partial view of the connector shown in FIG. 1.
Figure 3:
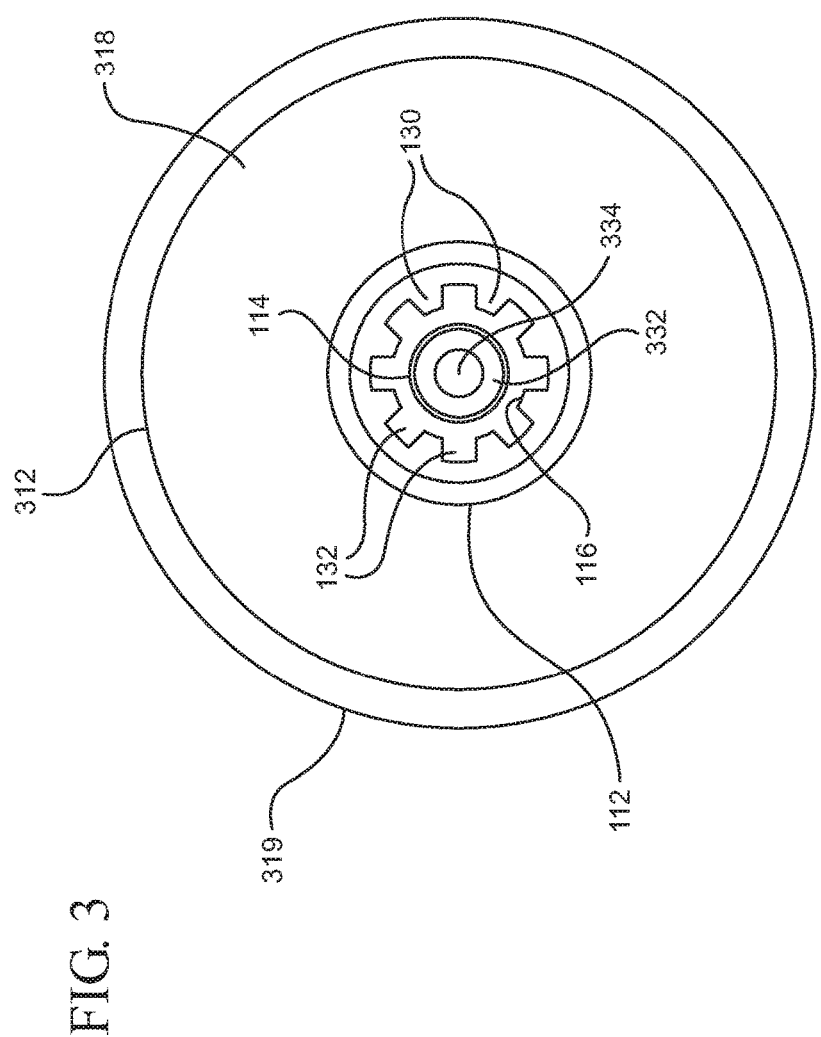
FIG. 3 shows a front elevational of the distal end of the connector.
Figure 4:
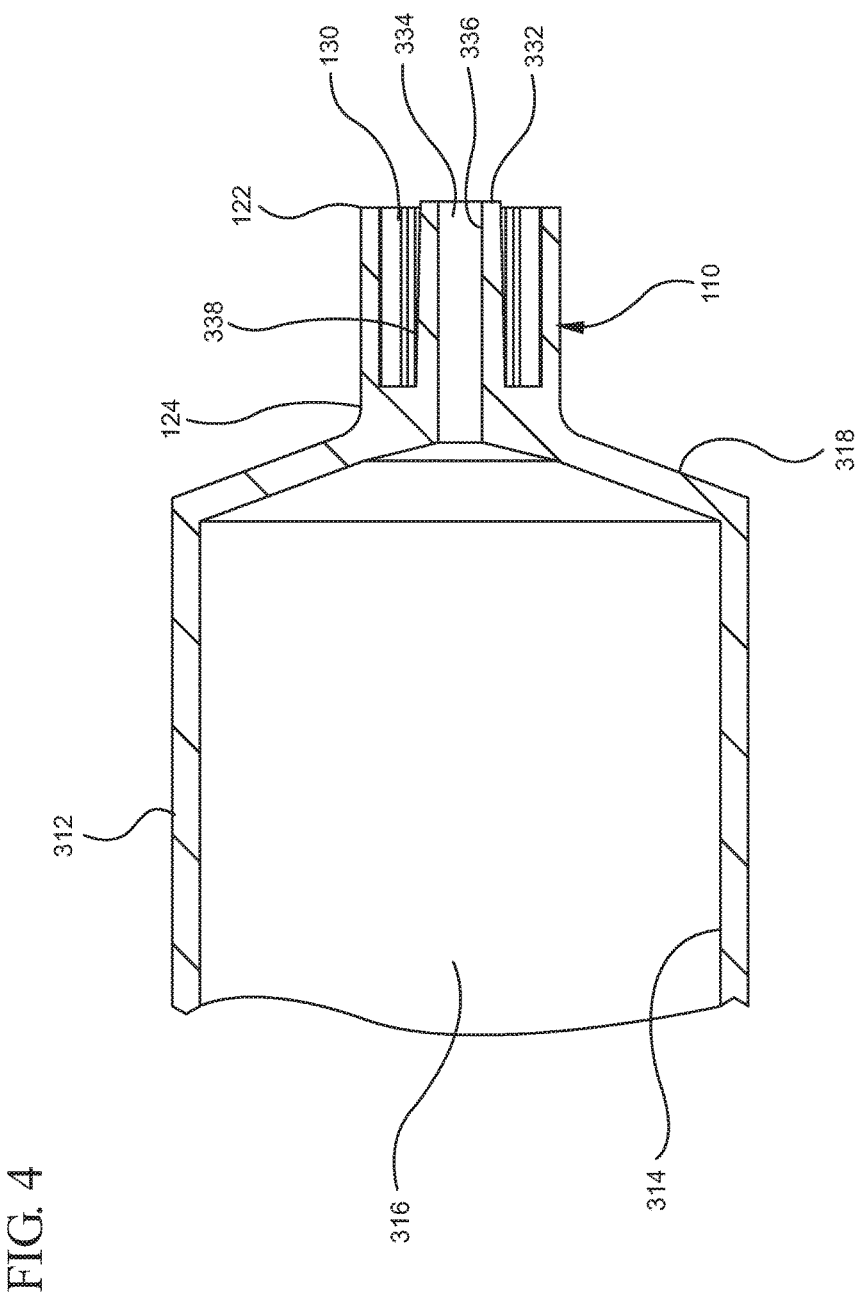
FIG. 4 illustrates a cross-sectional view of the connector shown in FIG. 2 taken along line 4-4.
Figure 5:
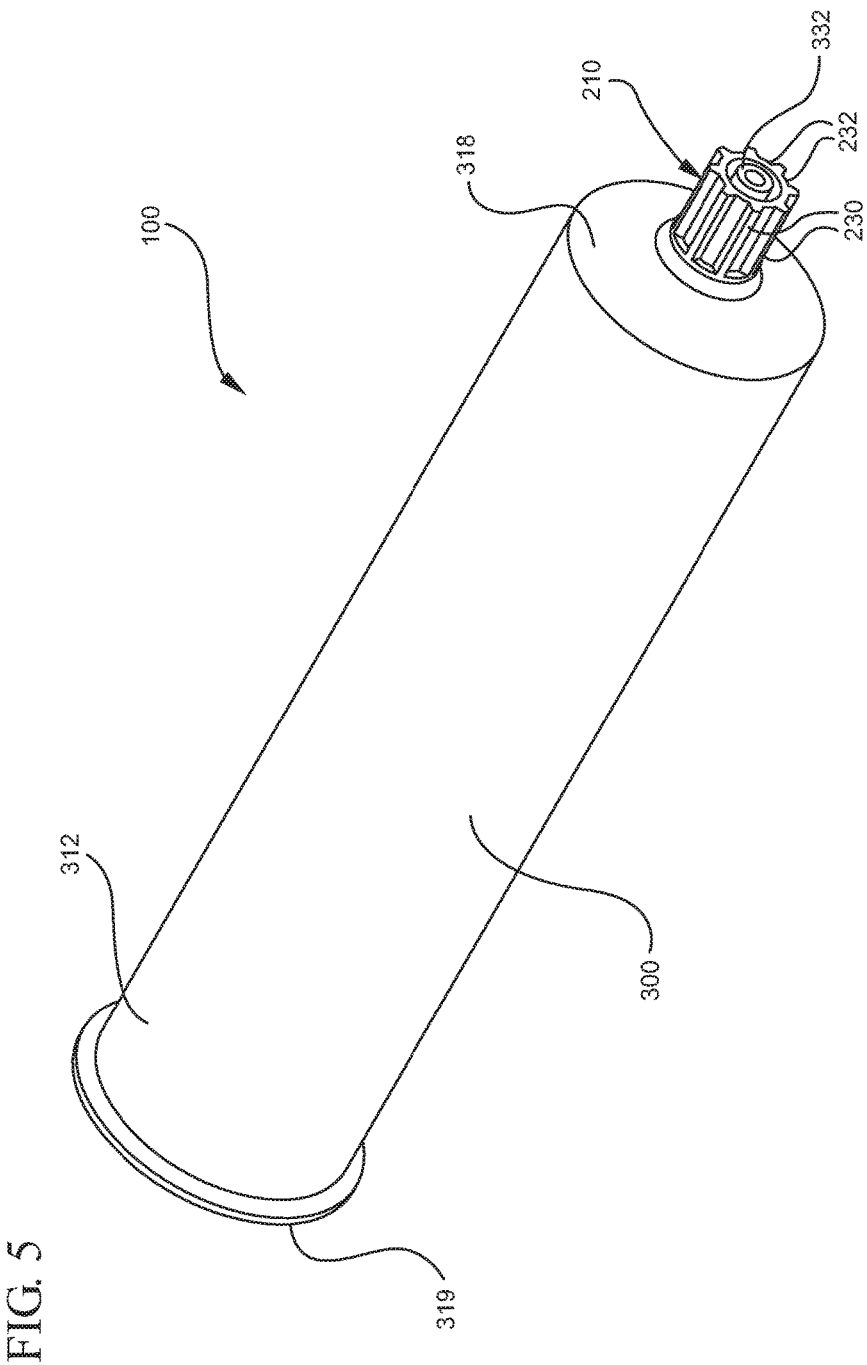
FIG. 5 illustrates a perspective view of a connector according to one or more embodiments.
Figure 6:
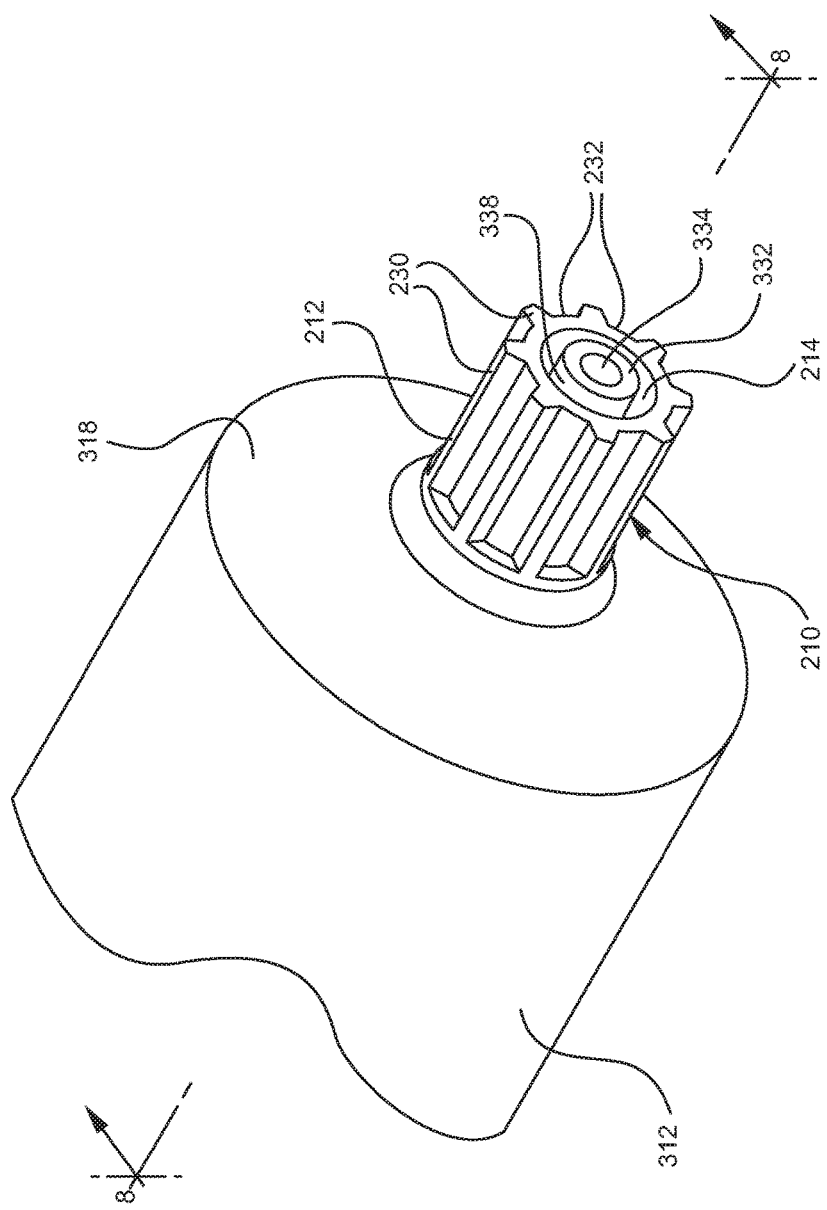
FIG. 6 illustrates an enlarged partial view of the connector shown in FIG. 1.
Figure 7:
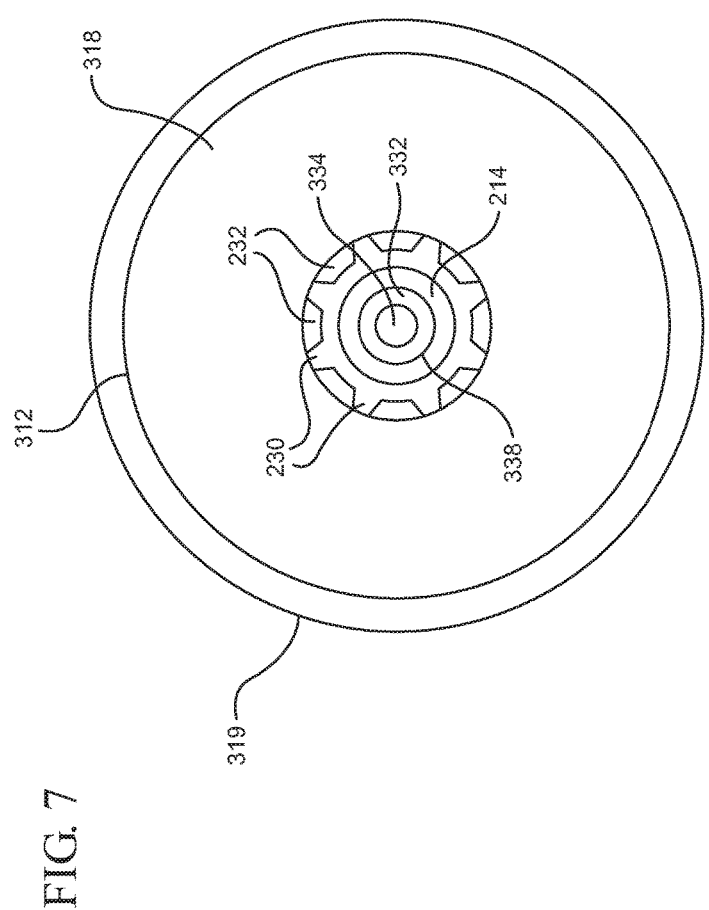
FIG. 7 shows a front elevational of the distal end of the connector.
Figure 8:
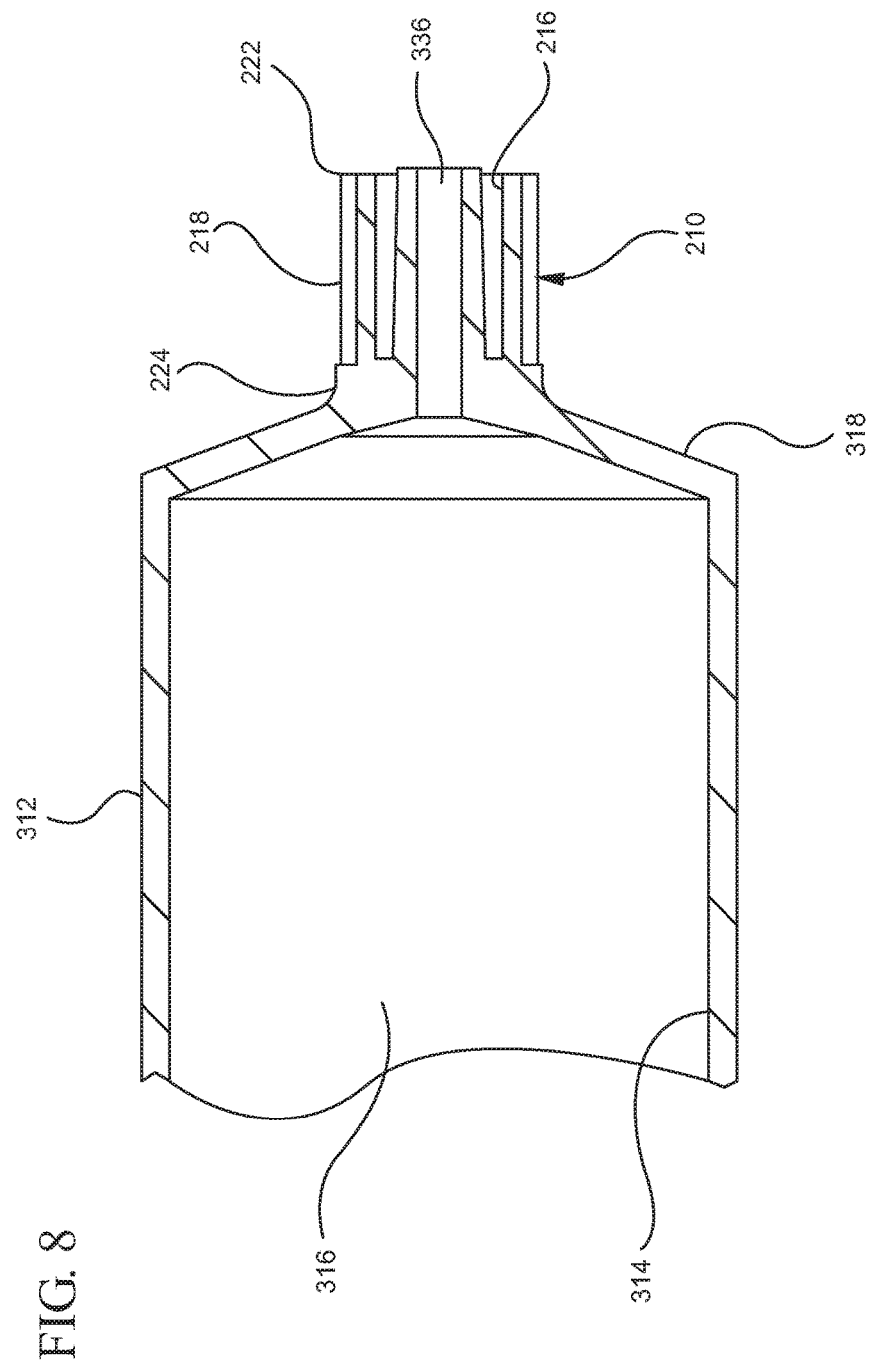
FIG. 8 illustrates a cross-sectional view of the connector shown in FIG. 6 taken along line 8-8.

Before describing several exemplary embodiments of the invention, it is to be understood that the invention is not limited to the details of construction or process steps set forth in the following description. The invention is capable of other embodiments and of being practiced or being carried out in various ways.

Aspects of the present invention pertain to male connectors that prevent misconnection to other non-compatible female connectors. A male connector shall be defined herein as a male connector that has a shape, size, dimension or structure that differs from a non-compatible female connector. Non-compatible female connectors may include standard female luer connectors, which conform to ISO 594-1:1986 and 594-2:1998, or non-luer female connectors, which do not conform to ISO 594-1:1986 and 594-2:1998.

In one or more embodiments, non-compatible female connectors may have a shape, size, dimension or structure that does not conform to ISO 594-1:1986 or ISO 594-2:1998. Such non-compatible female connectors may be described as non-luer female connectors. In such embodiments, the non-compatible female connector may have a shape, size, dimension or structure that prevents it from being characterized or defined as a female luer connector as defined above or according ISO 594-1:1986 or ISO 594-2:1998. In one or more specific embodiments, non-compatible female connectors may have length and/or cross-sectional diameter that differs from a female luer connector as defined above or according ISO 594-1:1986 or ISO 594-2:1998. In a more specific embodiment, the non-compatible female connector may have a taper that differs from a luer connector as defined above or according ISO 594-1:1986 or ISO 594-2:1998. In an even more specific embodiment, the non-compatible female connector may have a more gentle taper than a female luer connector as defined above or according ISO 594-1:1986 or ISO 594-2:1998, a cross-sectional diameter that is smaller than a female luer connector as defined above or according ISO 594-1:1986 or ISO 594-2:1998 and/or a longer length than a female luer connector as defined above or according ISO 594-1:1986 or ISO 594-2:1998.

In one or more embodiments, non-compatible female connectors may have a shape, size, dimension or structure that conforms to ISO 594-1:1986 or ISO 594-2:1998. Such non-compatible female connectors may be referred to as luer female connectors. In such embodiments, the non-compatible female connector may have a shape, size, dimension or structure that conforms to a female luer connector as defined above or according ISO 594-1:1986 or ISO 594-2:1998. In one or more specific embodiments, a non-compatible female connector may have length and/or cross-sectional diameter that are substantially the same as a female luer connector as defined above or according ISO 594-1:1986 or ISO 594-2:1998. In a more specific embodiment, a non-compatible female connector may have a taper that is substantially the same as a female luer connector as defined above or according ISO 594-1:1986 or ISO 594-2:1998.

The embodiments of the male connectors described herein incorporate features that prevent connection of a non-compatible female connector to the device on which the male connector is disposed or with which it is utilized. As used herein, the male connectors, compatible female connectors and non-compatible female connectors may include needle hubs, syringes or other delivery components that incorporate a connector for assembly of parts.

A first aspect of the present invention pertains to a male connector which has a shape, size and/or dimension that prevent connection of the male connector to a non-compatible female connector. One or more embodiments of a device 100 including a male connector are shown in FIGS. 1-8. The device 100 may be utilized as part of the drug delivery system. A first male connector 110 is shown in FIGS. 1-4 may be attached to the device 100 for connection to a corresponding or compatible female connector, for example, the compatible female connectors that will be described below. FIGS. 5-8 illustrate the device 100 including a second male connector 210 that may be connected to a corresponding or compatible female connector, as will be described below. The first and second male connectors 110, 210 may include an elongate tip and a collar disposed coaxially around the elongate tip. Both the first male connector 110 and the second male connector 210 have a shape, size or dimension that prevent connection of non-compatible female connectors to the device 100.

The first and second male connectors 110, 210 of FIGS. 1-8 are shown integrally formed to the device 100. The first and second male connectors 110, 210 may be provided as attachments or adapters that may be removably attached to the device 100. More specifically, the first and second male connectors 110, 210 may include an attachment mechanism for securing the connectors 110, 210 to the device 100, as shown in FIGS. 19-22. For example, the first and second male connectors 110, 210 may include a threaded portion (not shown) for attachment to a corresponding threaded portion (not shown) on the device 100. In one or more alternative embodiments, the first and second male connectors 110, 210 may include a snap fit structure for attachment to a corresponding structure on the device 100 such that the first and second male connectors 110, 210 are attached to the device 100 in a snap fit relationship. A third male connector 310, which will be described below, includes an adapter for attachment to a device with a standard male luer tip or standard male luer connector that, when attached to such a device, prevents connection of a standard female luer hub to the standard male luer tip. Embodiments of the third male connector 310 allow the user to utilize a syringe or other device including a standard male luer tip with connectors that do not conform to ISO 594-1:1986 or ISO 594-2:1998. Specifically, the third male connector 310 enables formation of a connection between a device including a standard male luer tip and a compatible female connector. The third male connector 310 also prevents connection between the device including a standard male luer tip and a non-compatible female connector.

In the embodiment shown, the device 100 is shown in the form of a syringe barrel 300. The device 100 may be provided in other forms, for example, a drug bag, an epidural pump and other containers known in the art. The syringe barrel 300 shown in FIGS. 1-13 includes a distal end 311, an open proximal end 319 and a sidewall 312 extending between the distal end 311 to the open proximal end 319. The sidewall 312 includes an inside surface 314 that defines a chamber 316 for retaining fluids, which may include liquid medication and/or other liquids, as more clearly shown in FIG. 8. The open proximal end 319 may include an optional flange. The distal end 311 includes a distal wall 318 an elongate tip 332 that extends in the distal direction from the distal wall 318. The elongate tip 332 includes an opening 334 providing access to the chamber 316. The elongate tip 332 includes an outside surface 338 and an inside surface 336 that defines a passageway 342 permitting fluid communication between the chamber 316 and the opening 334.

The elongate tip 332 forms part of the first male connector 110. In one or more embodiments, the elongate tip 332 may be sized or have dimensions in accordance with the proposed dimensions and size of ISO 80369-6 for neuraxial applications. Specifically, the outside surface 338 of the elongate tip 332 may have a taper of less than 6% or, more specifically, a taper of 5%. In other words, the outside surface 338 of the elongate tip 332 may have a cross-sectional diameter that decreases from the distal wall 318 to the opening 334 at a rate of less than 6% or at a rate of about 5%. In one or more embodiments, the elongate tip 332 may have a length that is greater than 0.295 inches (0.749 cm). In a more specific embodiment, the elongate tip 332 may have a length that conforms to the dimensions provided in ISO 80369-6 for neuraxial applications of about 0.300 inches (0.762 cm). In another variant, the outside surface 338 of the elongate tip 332 may have a cross-sectional diameter measured at the opening 334 of less than 0.1545 inches (0.3924 cm), or more specifically, in the range from about 0.1306 inches (0.3317 cm) to about 0.1326 inches (0.3368 cm).

In one or more embodiments, the elongate tip 332 may be sized or have dimensions in accordance with ISO 594-1:1986 or ISO 594-2:1998. In one or more specific embodiments, the elongate tip 332 may have a taper of about 6%. In other words, the outside surface 338 of the elongate tip 332 may have a cross-sectional diameter that decreases from the distal wall 318 to the opening 334 at a rate of 6%. In one or more embodiments, the elongate tip 332 may have a length of about 0.295 inches (0.749 cm). In another variant, the outside surface 338 of the elongate tip 332 may have a cross-sectional diameter measured at the opening 334 in the range from about 0.1545 inches (0.3924 cm) to about 0.1585 inches (0.4026 cm).

In addition to the elongate tip 332, the first male connector 110 also includes a collar 112 disposed coaxial around the elongate tip 332 and forming a channel 114 between the elongate tip 332 and the collar 112 for receiving a portion of a compatible female connector. The collar 112 includes an inside surface 116 and an outside surface 118. The collar 112 includes an inner diameter defined by a plurality of ribs 130 disposed on the inside surface 116 of the collar. The plurality of ribs 130 extend into the channel 114 and are separated by recesses 132. In one or more embodiments, the inside surface 116 may include two ribs separated by two spaces. In one or more alternative embodiments, the inside surface 116 may include three, four, five, six or more ribs separated by three, four, five, six or more spaces. In one or more variants, the inside surface 116 of the collar 112 may be free of any ribs 130. In such embodiments, the collar 112 has a thickness such that the inner diameter prevents connection of a non-compatible connector to the connector 110. The thickness of the collar 112 is measured from the outside surface 118 at one of the plurality of ribs 130 located at one end of the collar 112 to the outside surface 118 of another of the plurality of ribs 130 located at an opposite end of the collar 112. In other words, the thickness of the collar 112 is the greatest distance measured from rib-to-rib located on opposite ends of the collar 112.

In one or more embodiments, the inner cross-sectional dimension of the collar 112 is greater than 0.168 inches. In one or more specific embodiments, the inner cross-sectional dimension of the collar 112 is greater than 0.200 inches. In one or more specific embodiments, the inner cross-sectional dimension of the collar 112 is greater than 0.210 inches.

In one or more embodiments, the outer cross-sectional dimension of the collar 112 is less than 0.395 inches. In one or more specific embodiments, the outer cross-sectional dimension of the collar 112 is less than 0.356 inches. In one or more specific embodiments, the outer cross-sectional dimension of the collar 112 is less than 0.220 inches.

In the embodiment shown, each of the plurality of ribs 130 has a square cross-sectional diameter. Alternative embodiments may utilize ribs having a rounded cross-section. The plurality of ribs 130 may be described as longitudinal. In the embodiment shown, the plurality of ribs 130 extend from a distal end 122 of the collar to a proximal end 124 of the collar.

FIGS. 5-8 illustrate the second male connector 210 attached to the device 100. The second male connector 210 may be connected to a corresponding or compatible connector, for example, the female connectors that will be described below. The device 100 is shown in the form of a syringe barrel 300, as described above, but can be provided in other forms such as a drug bag, an epidural pump and other containers known in the art. As discussed above with reference to the first male connector 110, the second male connector 210 includes the elongate tip 332 and a collar coaxially disposed around the elongate tip 332.

The second male connector 210 shown in FIGS. 5-8 is integrally formed or provided in the device 100 but may be provided as a separate component that may be removably attached to the device 100. The second male connector 210 includes a collar 212 that is disposed coaxial around the elongate tip 332 to form a channel 214 between the elongate tip 332 and the collar 212. The channel 214 receives a portion of a compatible connector. The collar 212 includes an inside surface 216 and an outside surface 218. The collar 212 includes an inner diameter 220. The plurality of ribs 230 extend radially outwardly from the outside surface 218 and are separated by spaces 232. In one or more embodiments, the outside surface 218 may include two ribs separated by two spaces. In one or more alternative embodiments, the outside surface 218 may include three, four, five, six or more ribs separated by three, four, five, six or more spaces. In one or more variants, the outside surface 218 of the collar 212 may be free of any ribs 230. In such embodiments, the collar 212 has a cross-sectional diameter such that the inner diameter 220 prevents connection of a non-compatible female connector to the second male connector 210. The cross-sectional diameter of the collar 212 is measured from the outside surface 218 at one of the plurality of ribs 230 located at one end of the collar 212 to the outside surface 218 of another of the plurality of ribs 230 located at an opposite end of the collar 212. In other words, the cross-sectional diameter of the collar 212 is the greatest distance measured from rib-to-rib located on opposite ends of the collar 212.

In one or more embodiments, the inner cross-sectional dimension of the collar 112 is greater than 0.168 inches. In one or more specific embodiments, the inner cross-sectional dimension of the collar 112 is greater than 0.200 inches. In one or more specific embodiments, the inner cross-sectional dimension of the collar 112 is greater than 0.210 inches.

In one or more embodiments, the outer cross-sectional dimension of the collar 112 is less than 0.395 inches. In one or more specific embodiments, the outer cross-sectional dimension of the collar 112 is less than 0.356 inches. In one or more specific embodiments, the outer cross-sectional dimension of the collar 112 is less than 0.220 inches.

In the embodiment shown, each of the plurality of ribs 230 has a square cross-sectional diameter. Alternative embodiments may utilize ribs having a rounded cross-section. The plurality of ribs 230 may be described as longitudinal. In the embodiment shown, the plurality of ribs 230 extend from a distal end 222 of the collar to a proximal end 224 of the collar.

Figure 10:
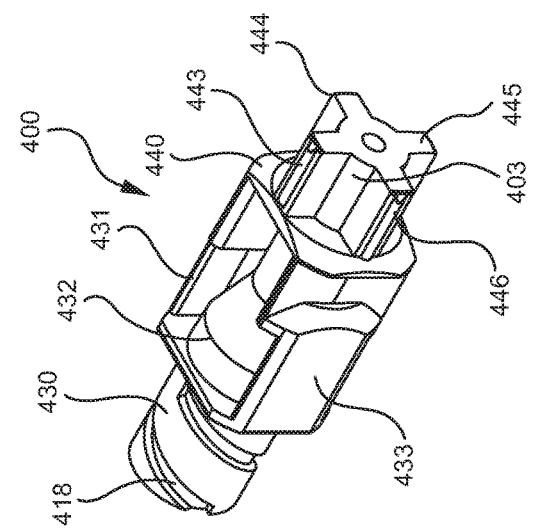
FIG. 10 shows a perspective view of the compatible connector shown in FIG. 9 taken from the distal end.
Figure 9:
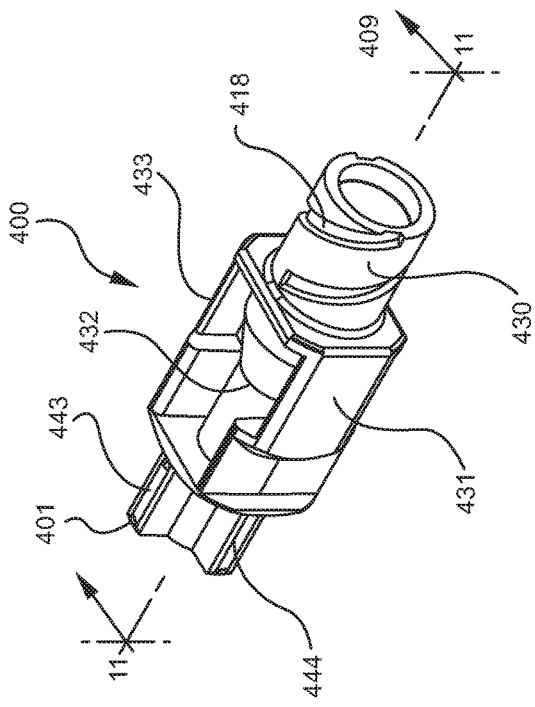
FIG. 9 illustrates a perspective view of a compatible connector according to one or more embodiments.

A compatible female connector 400 is shown in FIGS. 9-10 and includes an open distal end 401 and an open proximal end 409. The compatible female connector 400 also includes a hub body 432 including an attachment portion 430 for forming an interference fit connection with the first male connector 110 and/or the second male connector 210. The attachment portion 430 extends distally from the open proximal end 409 of the compatible female connector 400.

The hub body 432 and the attachment portion 430 include an inside surface 414 defining a cavity 416 for receiving at least a portion of a corresponding male connector. The compatible female connector 400 includes an outside surface 403 with a threaded portion 418 that is disposed along the entire circumference of the outside surface 403 and the entire length of the attachment portion 430 of the compatible female connector 400. The threaded portion 418 is utilized to engage a corresponding structure on the first male connector 110 and/or the second male connector 210, such as the threaded portion 234 of the second male connector 210.

In the embodiment shown, the inside surface 414 includes a first portion 412 extending from the open proximal end 409 to a second portion 413 that extends distally from the first portion 412 to a third portion 415. In one or more embodiments, the first portion 412 has a shape, size and/or dimension that enable engagement or attachment of the compatible female connector 400 with the first male connector 110 and/or the second male connector 210. In one variant, the inside surface 414 has a shape, size and/or dimension that forms an interference fit connection with the outside surface 338 of the elongate tip 332.

In one or more embodiments, the inside surface 414 has a shape, size and/or dimension that prevents engagement of the compatible female connector 400 to a male connector that has a shape, size and/or dimension that conforms to ISO 594-1:1986 and 594-2:1998. In one or more alternative embodiments, the inside surface 414 has a shape, size and/or dimension that prevents engagement of the compatible female connector 400 to a male connector that has a shape, size and/or dimension that does not conform to ISO 594-1:1986 and 594-2:1998. For example, the inside surface 414 may have a square, triangular or other non-circular cross-section that prevents the formation of an interference fit connection and/or fluid-tight engagement with an undesired connector.

In one or more embodiments, the compatible female connector 400 has a shape, size and/or dimension that prevents connection to a male connector that has a shape, size and/or dimension that conforms to ISO 594-1:1986 and 594-2:1998. In other words, the compatible female connector may have a shape, size and/or dimension that permits connection to a male connector having a shape, size and/or dimension that does not confirm to ISO 594-1:1986 and 594-2:1998. In such embodiments, the cavity 416 may have an inner cross-sectional diameter measured at the proximal end 409 of less than 0.168 inches. In one or more specific embodiments, the cavity 416 may have an inner cross-section dimension measured at the proximal end 409 in the range from about 0.100 inches to about 0.1600 inches, or more specifically in the range from about 0.1300 inches to about 0.1500 inches. In an even more specific embodiment, the cavity 416 has an inner cross-section dimension measured at the proximal end 409 in the range from about 0.1417 inches to about 0.1437 inches. In one or more embodiments, the inner cross-sectional diameter of the cavity 416 may be in the range from about 0.100 inches to 0.119 inches, from about 0.130 inches to about 0.139 inches, from about 0.140 inches to about 0.149 inches, from about 0.150 inches to about 0.159 inches, or from about 0.159 inches to about 0.167 inches. In one or more embodiments, the first portion 412 of the inside surface 414 may have a taper of less than 6% decreasing in a proximal to distal direction or an inner cross-section dimension that decreases from the proximal end 409 toward the distal end 401 at a rate of less than 6%. In one or more specific embodiments, the first portion 412 of the inside surface 414 has a taper decreasing in a proximal to distal direction in the range from about 3% to about 5.9%. In one or more embodiments, the taper of the first portion 412 of the inside surface 414 may be in the range from about 0.5% to about 4.9% decreasing in a proximal to distal direction. In a specific embodiment, the taper of the first portion 412 of the inside surface 414 is about 5% decreasing in a proximal to distal direction. In one or more embodiments, the length of the cavity 416 measured from the proximal end 409 to the end along the first portion 412 may be in the range from about 0.200 inches to about 0.500 inches. In a more specific embodiment, the length of the cavity 416 along the first portion 412 may be in the range from about 0.295 inches to about 0.400 inches. In an even more specific embodiment, the length of the cavity 416 along the first portion 412 may be about 0.303 inches.

In one or more embodiments, the compatible female connector 400 may have a shape, size or dimension that permits connection to a male connector that has a shape, size and/or dimension that conforms to ISO 594-1:1986 and 594-2:1998. In such embodiments the compatible female connector 400 may have a shape, size and/or dimension that permits prevents connection to a male connector that does not have a shape, size and/or dimension that conforms to ISO 594-1:1986 and 594-2:1998. In one or more variants, the cavity 416 may have an inner cross-sectional diameter measured at the proximal end 409 in the range from about 0.168 inches to about 0.170 inches. In one or more other variants, the inside surface 414 of the first portion 412 may have a taper of about 6% decreasing in a proximal to distal direction from the proximal end 409. Optionally, the length of the cavity 416 measured from the proximal end 409 along the first portion 412 may be about 0.295 inches.

The outside surface 403 of the compatible female connector 400 includes at least one arm that extends from the attachment portion 430 to a location adjacent to the open distal end 401 of the hub. In the embodiment shown in FIGS. 9-11, the compatible female connector 400 includes two arms 431, 433 that are disposed on opposite sides of the compatible female connector 400 and extend from the attachment portion 430 to a location adjacent to the open distal end 401. The arms 431, 433 define spaces between the outside surface 403 of the compatible female connector and the arms 431, 433. The arms 431, 433 provide a finger grip area or a gripping surface on which to grasp the compatible female connector 400 during use. The arms 431, 433 may have any shape known to provide such a finger grip area. In one or more alternative embodiments, the compatible female connector 400 may be free of any structure on its outside surface 403.

Figure 11:
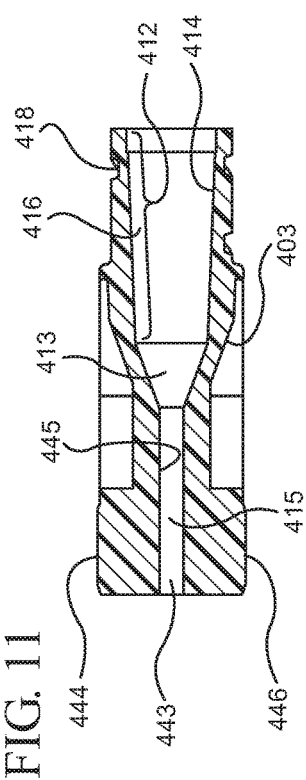
FIG. 11 illustrates a cross-sectional view of the compatible connector shown in FIG. 9, taken along line 11-11.

Adjacent to the open distal end 401, the compatible female connector includes an annular disc 440 disposed adjacent to the two arms 431, 432 that extends radially outwardly from the outside surface 403 of the hub. Four discrete protrusions 443, 444, 445, 446 extend radially outwardly from the outside surface 403 and extend from the annular disc 440 to the open distal end 401 along the same axis. The four discrete protrusions 443, 444, 445, 446 are located along the third portion 415, as shown in FIG. 11.

Figure 12:
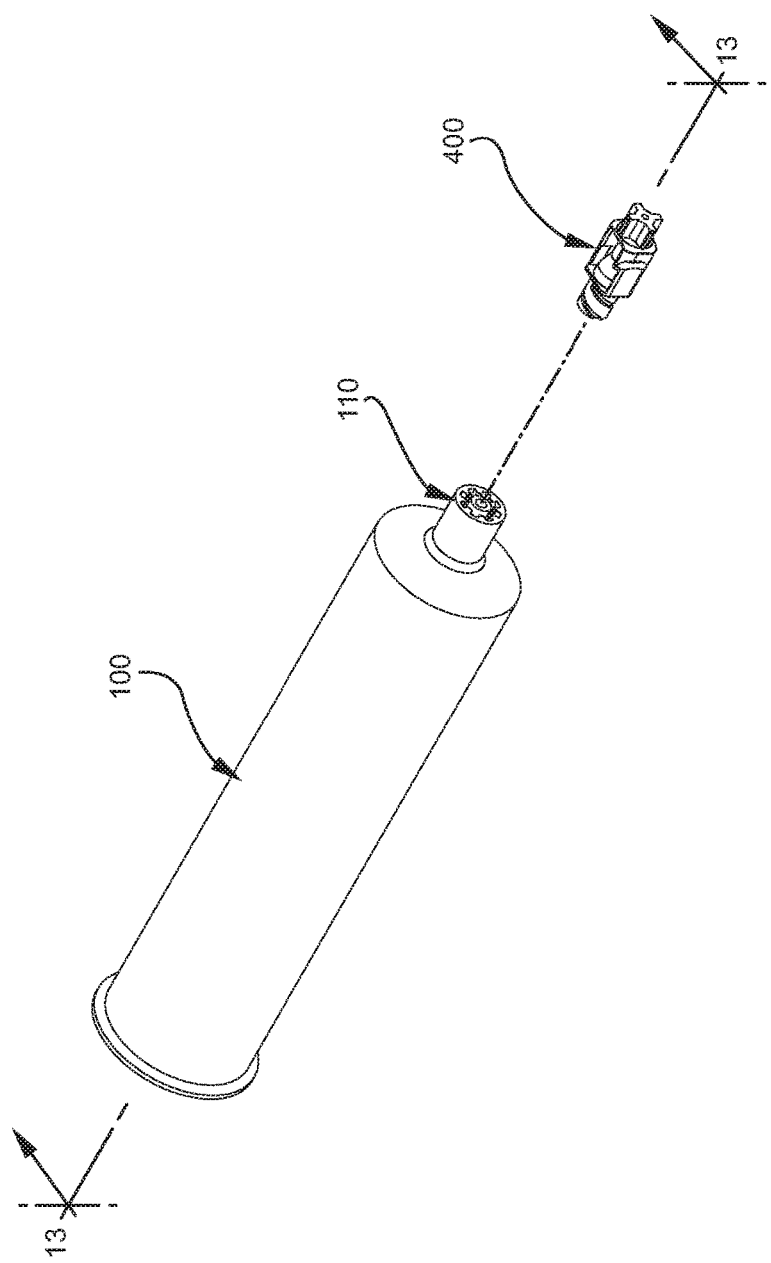
FIG. 12 illustrates an exploded perspective view of the male connector shown in FIG. 1 and the compatible connector shown in FIG. 9.
Figure 13:
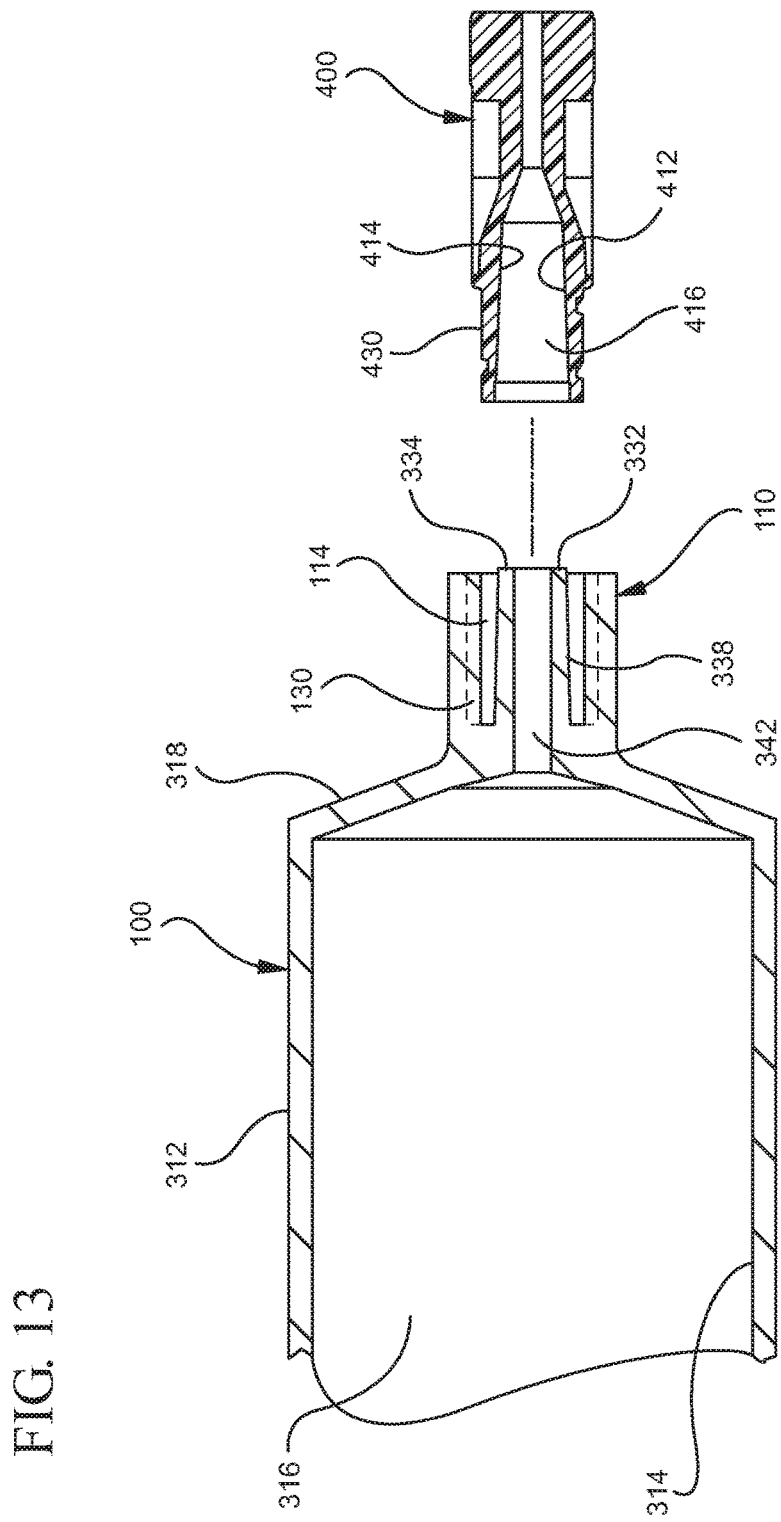
FIG. 13 is a cross-sectional view of the connector and compatible connector shown in FIG. 12 taken along line 13-13.
Figure 14:
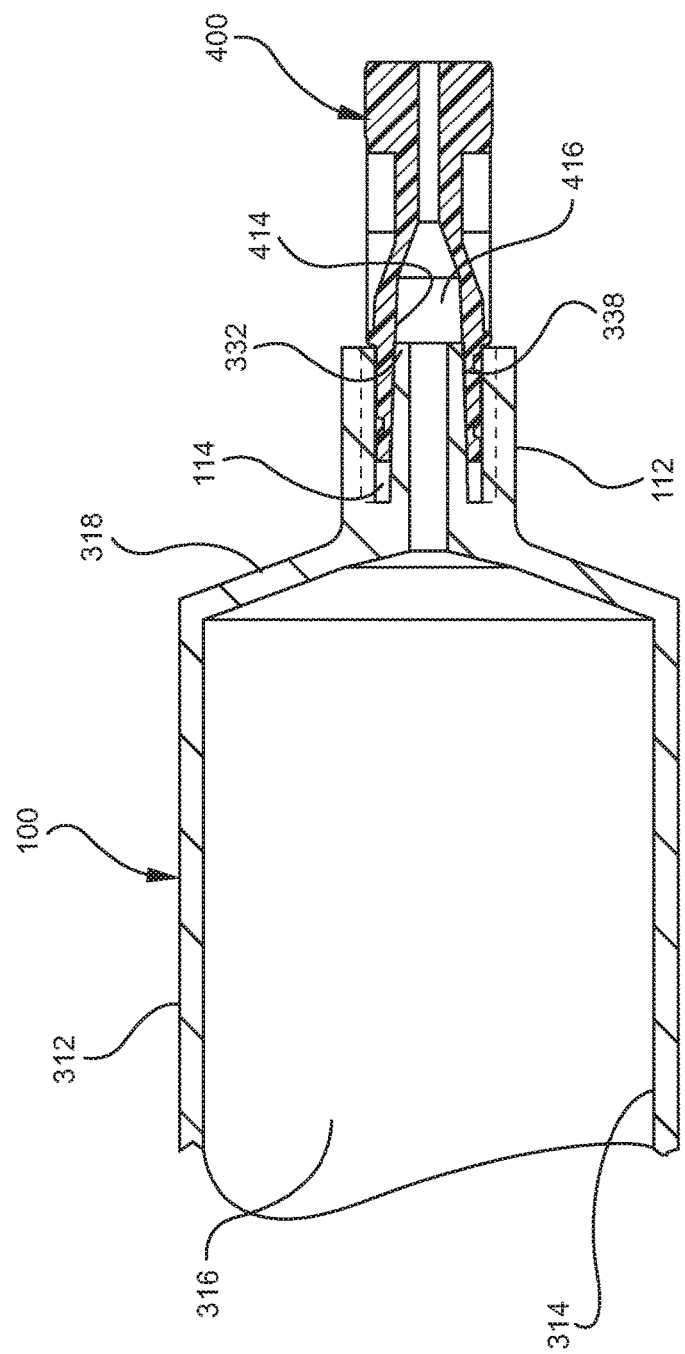
FIG. 14 illustrates a cross-sectional view of the connector assembled with the compatible connector shown in FIG. 9.
Figure 15:
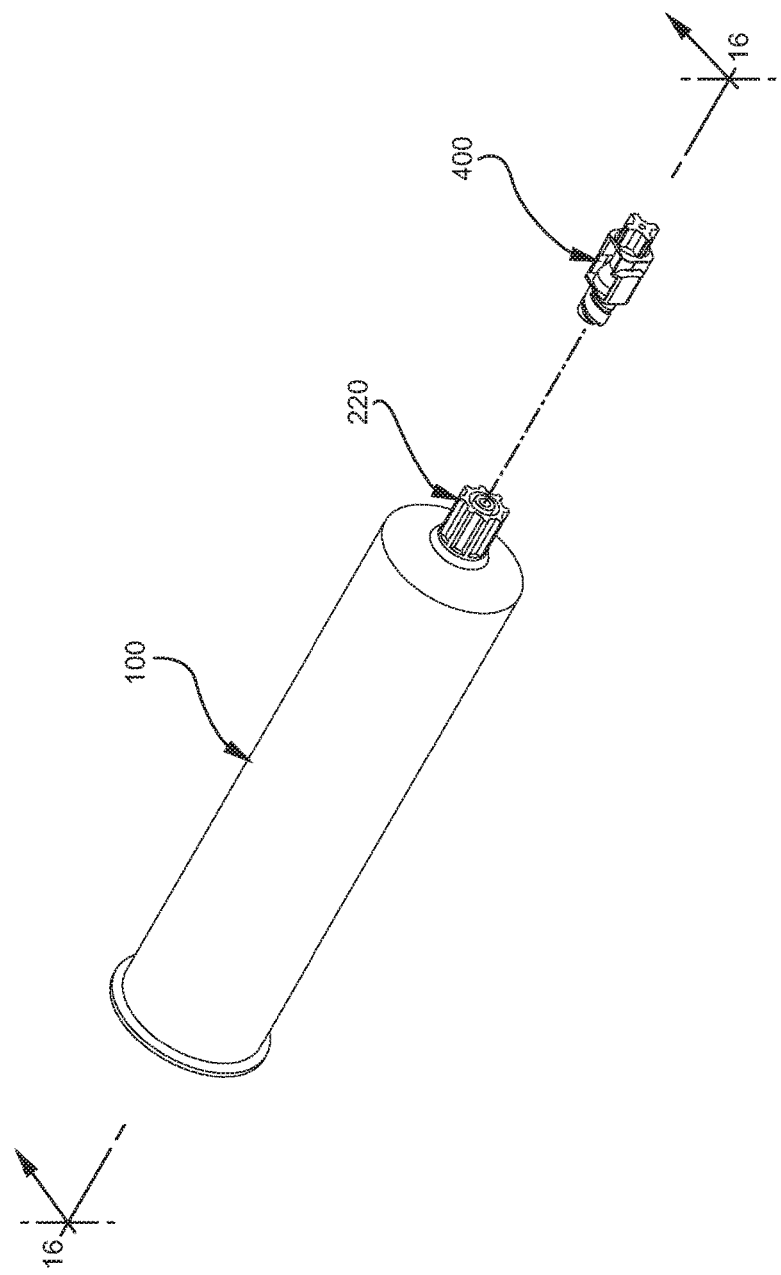
FIG. 15 illustrates an exploded perspective view of the connector shown in FIG. 5 and the compatible connector shown in FIG. 9.
Figure 16:
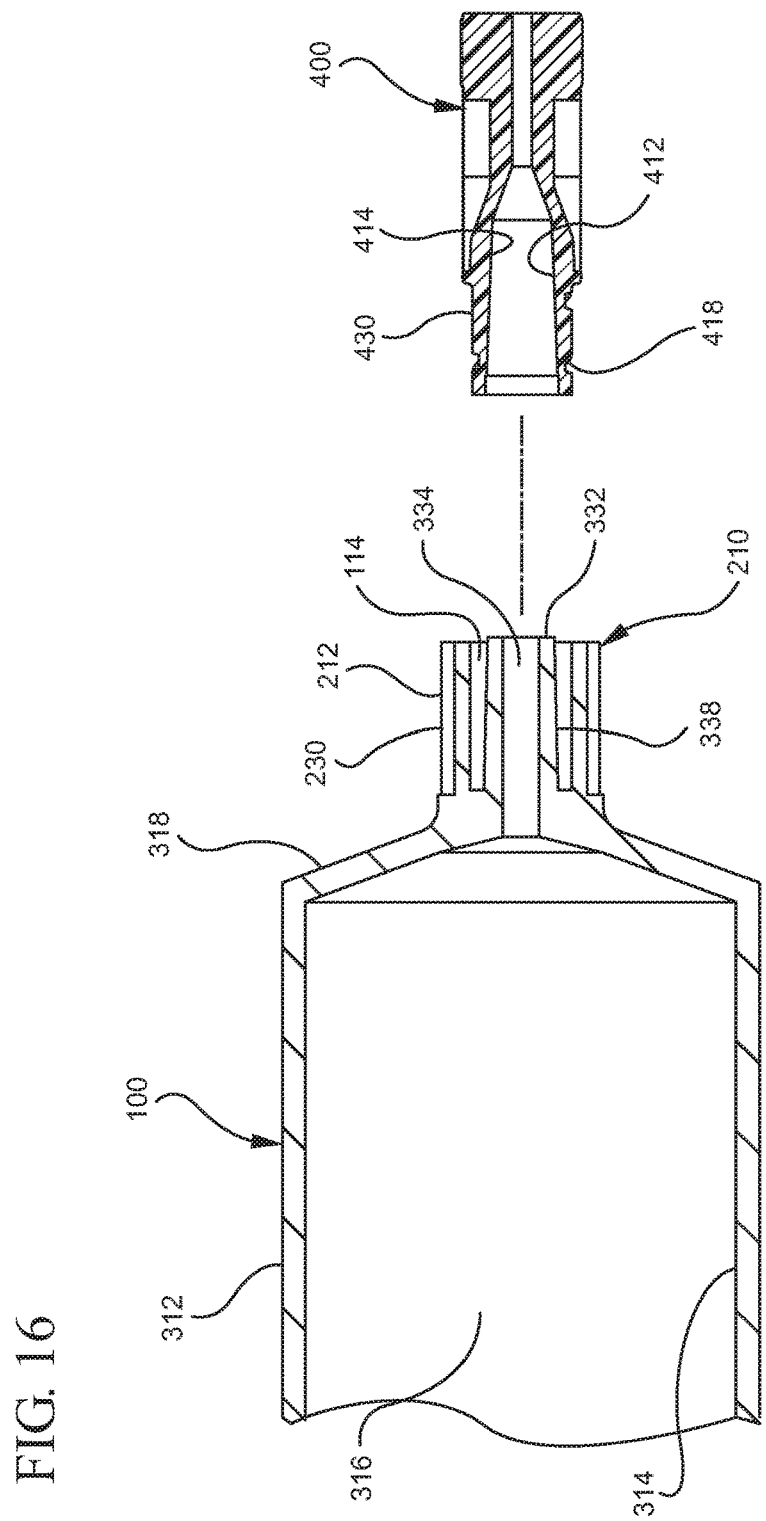
FIG. 16 is a cross-sectional view of the connector and compatible connector shown in FIG. 15 taken along line 16-16.
Figure 17:
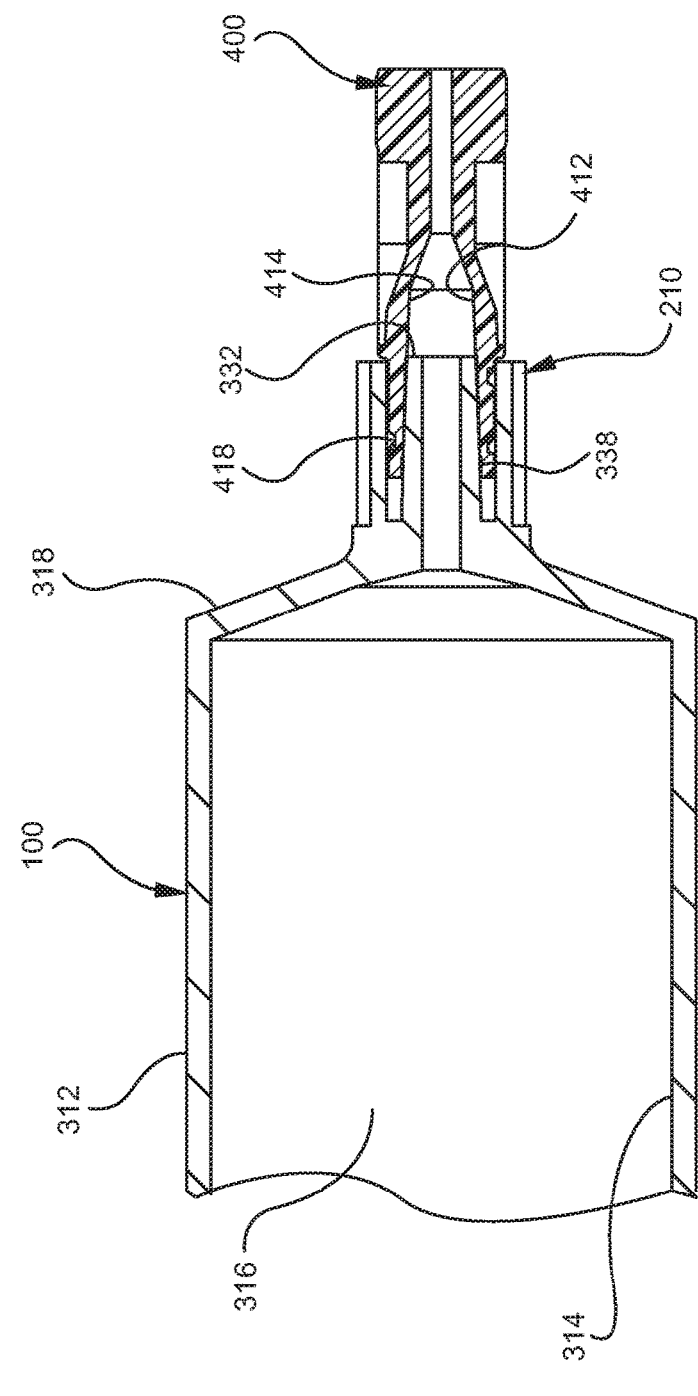
FIG. 17 illustrates a cross-sectional view of the connector assembled with the compatible connector shown in FIG. 9.

In one or more embodiments, the elongate tip 332 of the male connectors 110, 210 may be connected to the compatible female connector 400 in a luer slip configuration. As shown in FIGS. 12-14, a compatible female connector 400 may be assembled with the device 100 having the first male connector 110 by inserting the attachment portion 430 of the compatible female connector 400 into the channel 114 such that the inside surface 414 of the first portion 412 of the compatible connector is in contact with the outside surface 338 of the elongate tip 332 and forms a interference fit connection to the outside surface 338 of the elongate tip 332. Similarly, as shown in FIGS. 15-17, the compatible female connector 400 may be assembled with the device including the second male connector 210 by inserting the compatible female connector 400 into the channel 214 such that an inside surface 414 of the first portion 412 of the compatible connector is in contact with the outside surface 338 of the elongate tip 332 and forms a interference fit connection to the outside surface 338 of the elongate tip 332.

Figure 18:
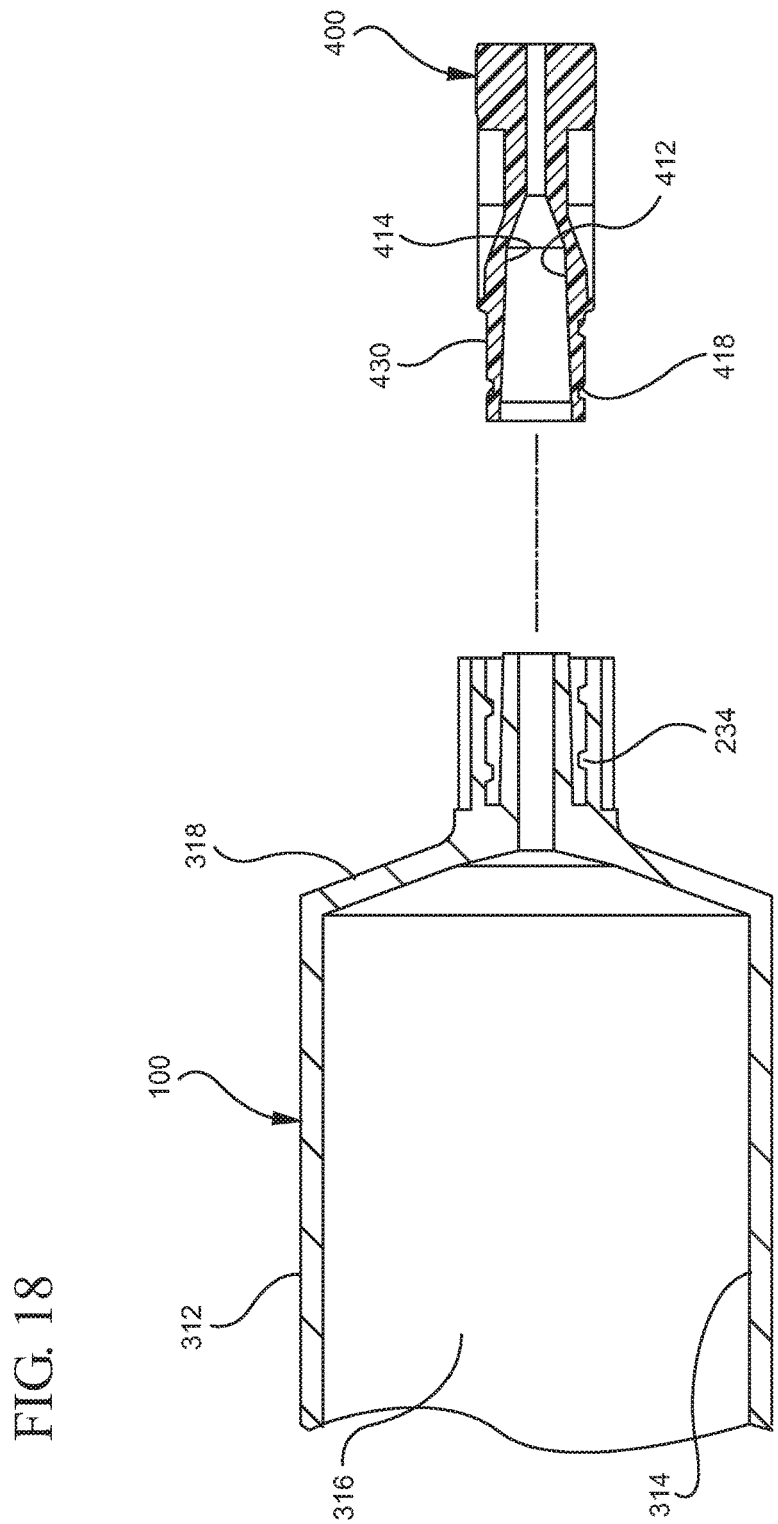
FIG. 18 illustrates a cross-sectional view of a connector according to one or more embodiments and the compatible connector shown in FIG. 9.

FIG. 18 illustrates an alternative embodiment of the second male connector 210. The second male connector 210 shown in FIG. 18 includes a threaded portion 234 to engage the threaded portion 418 of the compatible female connector 400 for attachment of the second male connector 210 and the compatible female connector 400 in a luer lock configuration. The compatible female connector 400 may also include a pair of lugs (not shown) disposed on its outside surface for engaging the threaded portion 234 of the second male connector 210. In such embodiments, the attachment portion 430 of the compatible female connector 400 may be inserted into the channel 214 and rotated around the elongate tip 332 such that the threaded portion 418 of the compatible female connector 400 engages the threaded portion 234 of the second male connector.

The first male connector 110 and the second male connector 210 prevent connection of non-compatible female connectors to the device 100. Specifically, the plurality of ribs 130, 230 of the first male connector 110 and the second male connector 210 increase the thickness of the wall of the collar 112, 212 such that a non-compatible female connector cannot enter the channel 114, 214. The increase in thickness of the wall of the collar 112, 212 increases the outer cross-sectional diameter of the collar 112, 212 and/or decreases the inner cross-sectional diameter of the collar 112, 212. In one or more embodiments, the collar 112, 212 may be shaped and/or sized to increase the outer cross-sectional diameter of the collar 112, 212 and/or decrease the inner cross-sectional diameter of the collar 112, 212. The increase in the outer cross-sectional diameter and the decrease in the inner cross-sectional diameter prevent a non-compatible female connector from entering the channel 114, 214 and forming a fluid-tight connection with the elongate tip 332.

In one or more embodiments, the presence of the plurality of ribs 130 on the inside surface 116 of the collar 112 in the first male connector 110 reduces the diameter of the channel 114 such that the diameter of a compatible female connector must be within a narrower range to fit within the channel 114 to form a fluid-tight connection with the elongate tip 332. In addition, the presence of the plurality of ribs 130 on the inside surface 116 of the collar 112 decreases the inner cross-sectional diameter of the collar 112 such that a non-compatible female connector cannot enter the channel 114 and engage the elongate tip 332. In embodiments in which the non-compatible female connector conforms to ISO 594-1:1986 and 594-2:1998 or, in other words, is a standard female luer connector, the plurality of ribs 130 on the inside surface 116 of the collar causes the inner cross-sectional diameter to be less than the outer cross-sectional diameter of a standard female luer connector. In such embodiments, the outer cross-section dimension of the collar 112 is greater than 0.168 inches, the inner cross-sectional dimension of a standard female luer connector.

The presence of the plurality of ribs 230 on the outside surface 218 of the collar 212 of the second male connector 210 prevents a non-compatible female connector from sliding over the outside surface 218 of the collar to form a connection with the outside surface 218 of the collar. In addition, the presence of the plurality of ribs 230 on the outside surface 218 of the collar 212 allows the collar 212 to be shaped or sized to have a smaller diameter such that it reduces the diameter of the channel 214. In such embodiments, the narrower channel 214 requires a compatible female connector to have a diameter that falls within a narrower range to fit within the channel 214 and, thus, form a fluid-tight connection with the elongate tip. In embodiments in which the non-compatible female connector conforms to ISO 594-1:1986 and 594-2:1998 or, in other words, is a standard female luer connector, the plurality of ribs 230 on the outside surface 218 of the collar causes the outer cross-sectional diameter to be greater than 0.168 inches, the inner cross-sectional diameter of a standard female luer connector. In such embodiments, the inner cross-section dimension of the collar 212 is less than the outer cross-sectional diameter of the standard female luer connector.

A second aspect of the present invention pertains to a third connector 500 that functions as an adapter to provide, on a standard male connector, a male connector that prevents misconnection of the standard male connector to non-compatible female connectors as defined herein. As shown in FIGS. 19-22, the third connector 500 may include an open distal end 501 and an open proximal end 509 in fluid communication with the distal end 501. A female portion 510 extends from the proximal end 509 to a male portion that extends from the female portion 510 to the distal end 501. The female portion 510 includes an elongate conduit 512 extends from the male portion to the open distal end 501. The elongate conduit includes an inside surface 514 defining a cavity 516 for receiving a male luer connector or an elongate tip of a standard syringe barrel. The inside surface 514 defines a cross-sectional diameter that is substantially similar to the inside surface of a female connector that conforms to a standard female luer connector or a female connector that conforms to ISO 594-1:1986 and 594-2:1998. Accordingly, the inside surface 514 of the elongate conduit 512 has a size, shape, dimension or structure that conforms to ISO 594-1:1986 or ISO 594-2:1998. Such female connectors may be referred to as luer female connectors and are configured to form a connection with the outside surface of a standard male connector that conforms to ISO 594-1:1986 and 549-2:1998, as described above.

The female portion 510 also includes an outside surface 517 and at least one radially outwardly extending tab 518 that have a size, shape, dimension or structure that permits engagement of the female portion 510 to a luer lock structure of a standard male connector that conforms specifically to ISO 594-2:1998. In particular, the at least one radially outwardly extending tab 518 engages the threads disposed on an inside surface of luer lock structure of a standard male connector that conforms specifically to ISO 594-2:1998.

Figure 19:
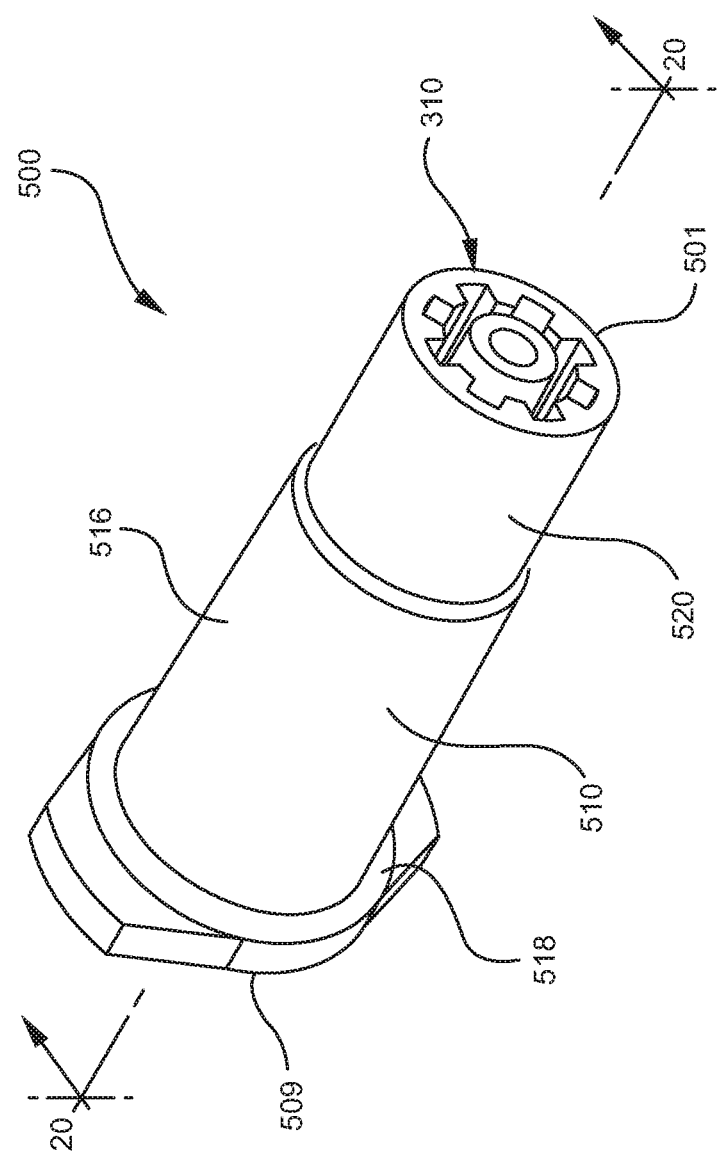
FIG. 19 illustrates a perspective view of a compatible connector according to one or more embodiments of the present invention.
Figure 20:
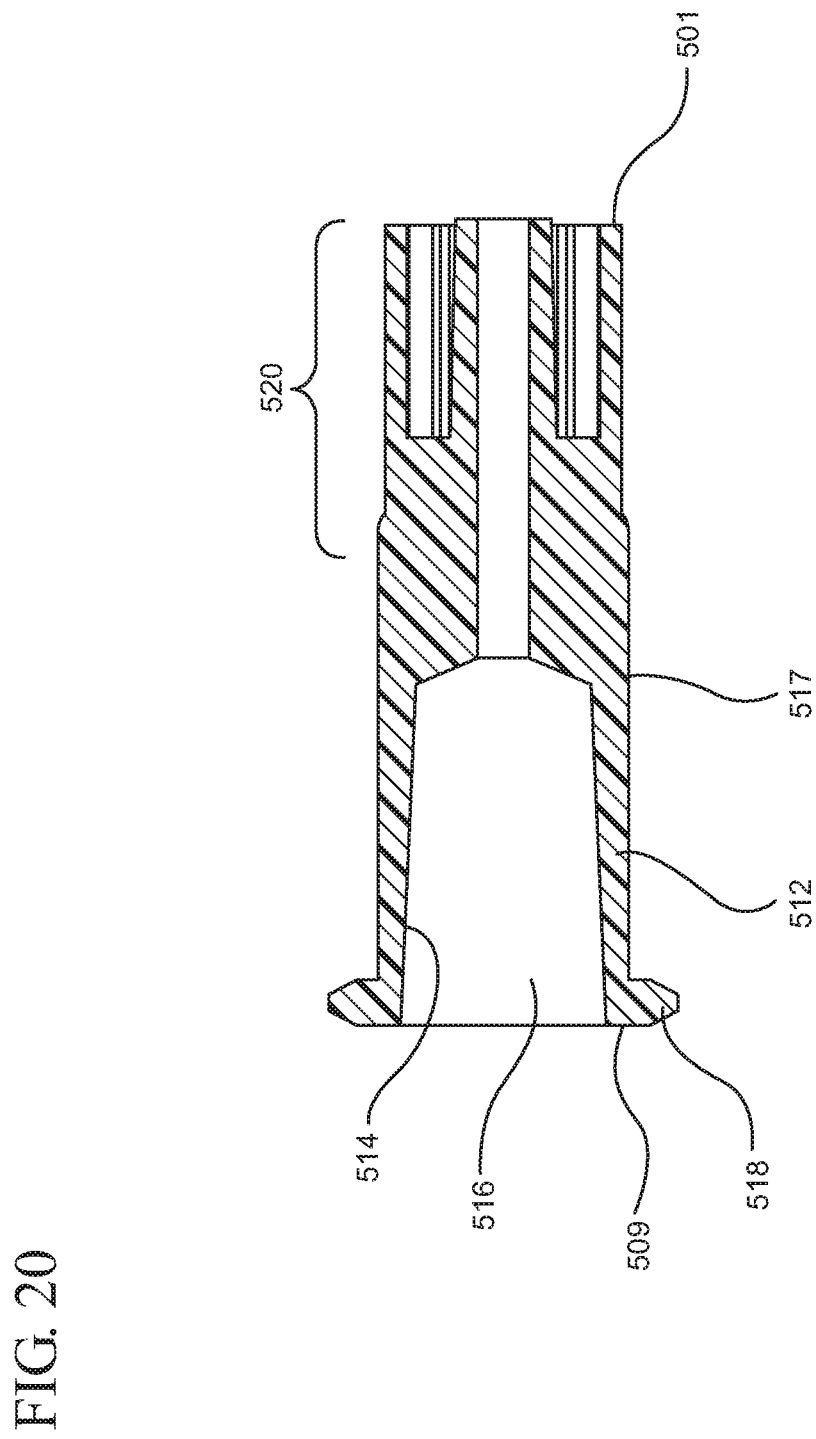
FIG. 20 illustrates a cross-sectional view of the connector shown in FIG. 19.
Figure 21:
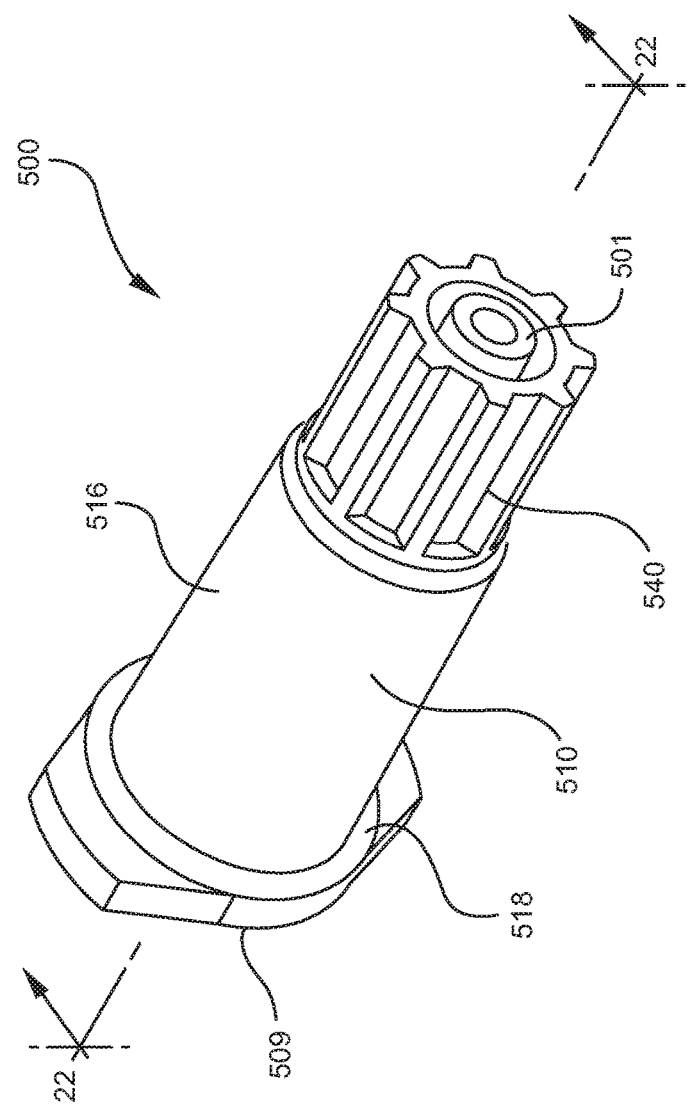
FIG. 21 illustrates a perspective view of a compatible connector according to one or more embodiments of the present invention.
Figure 22:
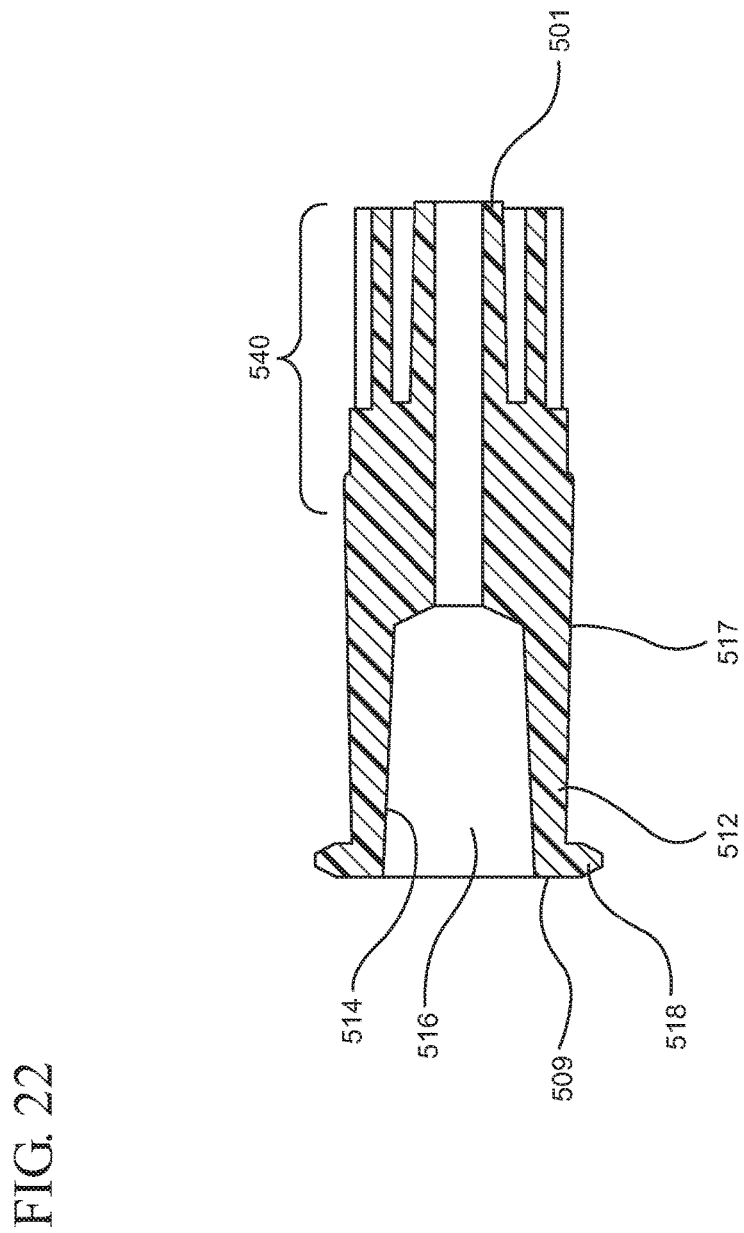
FIG. 22 shows a cross-sectional view of the connector shown in FIG. 21.

FIGS. 19-20 include a first male portion 520 that has a size, shape and dimension of the first male connector 110 shown in FIGS. 1-4. FIGS. 21-22 include a second male portion 540 that has a size, shape and dimension of the second male connector 210 illustrated in FIGS. 5-8.

In use, the third connector 500 may be attached to a drug delivery device including a standard male connector that conforms to ISO 594-1:1986 and 549-2:1998, as described above. Such standard male connectors include an elongate tip that extends from the drug delivery device and has an outside surface. In particular, the female portion 510 is placed over the outside surface of the elongate tip of the standard male connector until connection is formed between the female portion 510 and the standard male portion. In one or more embodiments, the connection may include an interference fit connection between the outside surface of the standard male connector and the inside surface 514 of the female portion 510. In one or more embodiments, the connection may include an interference fit connection between the inside surface of a luer lock structure of a standard male connector and the at least one radially outwardly extending tab 518. Such interference fit connection between the inside surface of a luer lock structure of a standard male connector and the at least one radially outwardly extending tab 518 may be established by inserting the elongate tip of the standard male connector into the cavity 516 of the female portion 510 and rotating the standard male connector and/or third connector 500 with respect to each other such that the at least one radially outwardly extending tab 518 engages the threaded portion disposed on the inside surface of the luer lock structure of the standard male connector.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A connector comprising:
an open distal end, a proximal end for attachment to a container, and an elongate tip having a taper less than 6% extending in a distal direction;
a collar coaxially disposed around the elongate tip to form a channel between the elongate tip and the collar, the collar including a plurality of longitudinal ribs disposed on an inside surface of the collar and extending inwardly into the channel formed between the collar and the elongate tip each of, the plurality of longitudinal ribs extend in a straight line in a longitudinal direction from an open distal end of the collar to a proximal end of the collar to provide an inner cross-sectional diameter of the collar that is greater than 0.168 inches and an outer cross-sectional dimension of the collar that is less than 0.395 inches which prevent entry of a non-compatible female connector into the channel and connection to the elongate tip.

2. The connector of claim 1, wherein the proximal end of the connector comprises a standard female luer hub.

3. The connector of claim 1, wherein the inner cross-sectional diameter being less than an outer cross-sectional diameter of a standard female luer connector.

4. The connector of claim 1, wherein the plurality of longitudinal ribs have a square cross-section.

5. The connector of claim 1, wherein the plurality of longitudinal ribs have a rounded cross-section.

6. The connector of claim 1, wherein the connector is configured for use in an enteral delivery system.

7. The connector of claim 1, wherein the connector is configured for use in a neuraxial delivery system.

8. A device comprising:
   a syringe barrel having a distal end, an open proximal end, a sidewall extending between the distal end to the open proximal end, the sidewall defining a chamber, the distal end of the syringe barrel includes a distal wall, and
   a connector of claim 1.

9. The device of claim 8, wherein the connector is configured for use in an enteral delivery system.

10. The device of claim 8, wherein the connector is configured for use in a neuraxial delivery system.

11. The device of claim 8, wherein the plurality of longitudinal ribs have a square cross-section.

12. The device of claim 8, wherein the plurality of longitudinal ribs have a rounded cross-section.

* * * * *